(12) United States Patent
Peukert et al.

(10) Patent No.: US 7,795,278 B2
(45) Date of Patent: Sep. 14, 2010

(54) SUBSTITUTED TETRAHYDRO-2H-ISOQUINOLIN-1-ONE DERIVATIVES, AND METHODS FOR THE PRODUCTION AND USE THEREOF

(75) Inventors: Stefan Peukert, Arlington, MA (US); Stefan Guessregen, Wiesbaden (DE); Armin Hofmeister, Dexheim (DE); Herman Schreuder, Hofheim-Lorsbach (DE); Uwe Schwahn, Sulzbach (DE)

(73) Assignee: sanofi-aventis Deutschland GmbH, Frankfurt am Main, DE (US)

( * ) Notice: Subject to any disclaimer, the term of this patent is extended or adjusted under 35 U.S.C. 154(b) by 862 days.

(21) Appl. No.: 11/567,352

(22) Filed: Dec. 6, 2006

(65) Prior Publication Data
US 2007/0142430 A1 Jun. 21, 2007

Related U.S. Application Data
(63) Continuation of application No. PCT/EP2005/005871, filed on Jun. 1, 2005.

(30) Foreign Application Priority Data
Jun. 16, 2004 (DE) .................. 10 2004 028 973

(51) Int. Cl.
C07D 217/22 (2006.01)
A61K 31/47 (2006.01)
(52) U.S. Cl. ........................ 514/309; 546/114
(58) Field of Classification Search .......... None
See application file for complete search history.

(56) References Cited

U.S. PATENT DOCUMENTS
3,594,380 A 7/1971 Sulkowski

FOREIGN PATENT DOCUMENTS
| EP | 0355750 | 2/1990 |
|---|---|---|
| WO | WO 99/11624 | 3/1999 |
| WO | WO 02/090334 | 11/2002 |

OTHER PUBLICATIONS
Rigby, et al., Nucleophilic Addition of Silyl Enol Ethers to Aromatic Nitro Compounds, J. of Organic Chem.; 49:23; 1984; pp. 4571-4572.
Rigby, et al., Perparation of Highly Substituted 2-Pyridones by Reaction of Vinyl Isocyanates and Enamines, J. of Organic Chem.; 54:1; 1989; pp. 224-228.

*Primary Examiner*—Zinna N Davis
(74) *Attorney, Agent, or Firm*—Serena Farquharson-Torres

(57) ABSTRACT

This invention relates to compounds according to the general formula (I), where the definitions of the substituents R1, R2, Ar and X are as specified in the description, and to their physiologically tolerated salts, methods for the preparation of these compounds and their use as medicaments.

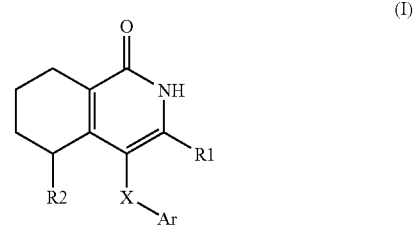

(I)

These compounds are poly(ADP-ribose) polymerase (PARP) inhibitors.

10 Claims, No Drawings

SUBSTITUTED TETRAHYDRO-2H-ISOQUINOLIN-1-ONE DERIVATIVES, AND METHODS FOR THE PRODUCTION AND USE THEREOF

FIELD OF THE INVENTION

This application is a CON of PCT/EP05/05871 filed Jun. 1, 2005.

The invention relates to compounds according to the general formula (I), where the definitions of the substituents R1, R2, Ar and X are as specified in the following text, and to their physiologically tolerated salts, methods for the preparation of these compounds and their use as medicaments.

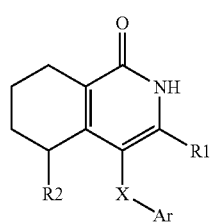

(I)

These compounds are poly(ADP-ribose) polymerase (PARP) inhibitors.

BACKGROUND OF THE INVENTION

Inhibitory Effect on PARP

Poly(adenosine 5'-diphosphate-ribose) polymerase [poly (ADP-ribose) polymerase, PARP], which is also known as poly(ADP-ribose) synthetase (PARS), is a chromatin-bound nuclear enzyme of eukaryotic cells, of which approximately $2 \times 10^5$ molecules are present per nucleus. PARP is, according to the most recent research results, involved in the pathogenesis of various disorders, and thus inhibition of PARP enzyme activity may have beneficial effects on the course of disorders in preclinical animal models (Cristina Cosi, Expert Opin. Ther. Patents, 2002, 12, 1047-1071 and L. Virag and C. Szabo, Pharmacol. Rev., 2002, 54, 1-54). Poly(ADP-ribose) polymerase occurs in all eukaryotic organisms with the exception of yeast, and is part of the genome surveillance network to protect the genetic information from genotoxic influences. DNA damage induces the enzymatic activity of poly(ADP-ribose) polymerase, leading under physiological conditions to repair of the errors recognized by the enzyme in the DNA. However, in pathological situations, poly(ADP-ribose) polymerase may be strongly activated by free-radical oxygen species—as is the case in ischemia, hypoxia, reperfusion or in inflammatory processes—resulting in consumption by the enzyme of large amounts of its substrate NAD. This depletion of NAD is one of the reasons for the death of cells to be observed in the affected tissue (the so-called energy crisis theory). The therapeutic use of PARP inhibitors is in the prevention or reduction of this NAD depletion in tissue. Apart from the role, described herein, in signal transmission ranging from oxidative stress in cells to NAD depletion, further cellular functions of PARP are suggested in the current literature, and these might likewise play a role in the molecular mechanism of action of PARP inhibitors in pathological situations (A. Chiarugi, Trends Pharmacol. Sci., 2002, 23, 122-129). Irrespective of this unresolved discussion about the molecular mechanism of action, the therapeutic efficacy of various PARP inhibitors has been shown in several preclinical animal models: thus, for example, for acute myocardial infarction, acute renal failure, cerebral ischemia (stroke), neurodegenerative disorders (e.g. a model of Parkinson's disease), diabetes, xenobiotic-induced hepatotoxicity, arthritis, shock lung, septic shock and as sensitizer in the chemotherapy of neoplastic disorders (summarized in L. Virag and C. Szabo, Pharmacol. Rev., 2002, 54, 1-54).

It has specifically been possible to show that PARP inhibitors bring about morphological and functional improvements not only in acute myocardial infarction (J. Bowes et al., Eur. J. Pharmacol., 1998, 359, 143-150; L. Liaudet et al., Br. J. Pharmacol., 2001, 133, 1424-1430; N. Wayman et al., Eur. J. Pharmacol., 2001, 430, 93-100), but also significantly better cardiac functions have been measured in chronic heart failure during PARP inhibitor treatment (P. Pacher, J. Am. Coll. Cardiol., 2002, 40, 1006-1016). The hypoperfusion like that which, in the infarcted heart, brings about losses of function of the organ through death of cells also appears in stroke at the start of the chain of events which leads to losses or complete failure of individual regions, and thus functions, of the organ. Accordingly, it has been possible to show the efficacy of PARP inhibitors—besides the genetic ablation of the PARP-1 gene (M. J. L. Eliasson et al., Nat. Med., 1997, 10, 1089-1095)—also in models of cerebral ischemia (K. Takahashi et al., J. Cereb. Blood Flow Metab., 1997, 11, 1137-1142), of MPTP-induced neurotoxicity (C. Cosi et al., Brain Res., 1996, 729, 264-269) and of neuronal excitotoxicity (A. S. Mandir et al., J. Neurosci., 2000, 21, 8005-8011). A further finding which is very important in connection with cardiovascular disorders is the efficacy of PARP inhibition in the ischemically damaged kidney, where improvements in the filtration function of the organ have likewise been found in animals treated with PARP inhibitors compared with those treated with placebo (D. R. Martin et al., Am. J. Physiol. Regulatory Integrative Comp. Physiol., 2000, 279, R1834-R1840). In contrast to the acute ischemic insults of the above-mentioned disorders, chronic PARP activation occurs in various pathologies such as, for example, in diabetes. The efficacy of PARP inhibitors has been demonstrated both in preclinical models of type I diabetes (W. L. Suarez-Pinzon et al., Diabetes, 2003, 52, 1683-1688) and in those of type II diabetes (F. G. Soriano et al., Nat. Med., 2001, 7, 108-113; F. G. Soriano et al., Circulation, 2001, 89, 684-691). The beneficial effect of PARP inhibitors in type I diabetes is attributable to their antiinflammatory properties, which it has also been possible to show in further preclinical models, such as of chronic colitis (H. B. Jijon et al., Am. J. Physiol. Gastrointest. Liver Physiol., 2000, 279, G641-G651), of collagen-induced arthritis (H. Kröger et al., Inflammation, 1996, 20, 203-215) and in septic shock (B. Zingarelli et al., Shock, 1996, 5, 258-264). In addition, PARP inhibitors have a sensitizing effect on tumors in chemotherapy on mice (L. Tentori et al., Blood, 2002, 99, 2241-2244).

Background References

It has been disclosed in the literature (for example C. Cosi, Expert Opin. Ther. patents, 2002, 12, 1047-1071; Southan et al., Current Medicinal Chemistry, 2003, 10, 321-340) that many different classes of chemical compounds can be used as PARP inhibitors, such as, for example, derivatives of indoles, benzimidazoles, isoquinolinols or quinazolinones. Many of the previously disclosed PARP inhibitors are derivatives of a bi- or polycyclic basic structure.

The use of isoquinolinone derivatives as PARP inhibitors is described for example in WO 02/090334. The isoquinolinone derivatives described therein are without exception based on a basic structure in which the second ring of the bicycle (with carbon atoms 5, 6, 7 and 8) is in aromatic form, whereas the ring having the amide group of the bicycle may optionally be hydrogenated in position 3 and 4. The isoquinolinone derivatives disclosed in EP-A 0 355 750, which can likewise be used as PARP inhibitors, are based on the same aromatic basic structure.

A large number of PARP inhibitors can be inferred from the general formula (I) disclosed in WO 99/11624. Disclosed therein inter alia is a tetrahydro-2H-isoquinolin-1-one derivative which has an aminoethyl substituent in position 4. A further possibility is for the radical $R^6$ in formula (I) also to be aryl, although it is not mentioned that this aryl radical optionally has further substituents. An aryl radical for $R^6$ is specifically described in WO 99/11624 only for examples in which the ring defined by Y in the basic structure both is unsaturated and has heteroatoms. The specific combination of a 5,6,7,8-tetrahydro-2H-isoquinolin-1-one derivative which is substituted in position 4 either directly or via a linker by an aryl or heteroaryl radical is, however, neither disclosed in nor obvious from WO 99/11624. It is thus evident that the compounds of the invention are not disclosed by WO 99/11624. The present invention does not relate to compounds as such which are explicitly disclosed in WO 99/11624.

J. Rigby et al., J. Org. Chem. 1984, 4569-4571, describe, within the framework of a general synthetic method for the cyclization of vinyl isocyanates, the preparation of 4-phenyl-5,6,7,8-tetrahydro-2H-isoquinolin-1-one by cyclocondensation of an enamine and of a vinyl isocyanate. No association is made between the compounds described in J. Rigby et al. and any use as pharmaceuticals. The present invention does not relate to the compounds explicitly disclosed by J. Rigby et al. as such.

SUMMARY OF THE INVENTION

Since diseases, such as myocardial infarction, which can be treated by inhibition of PARP represents a serious risk for the health of humans and other mammals, there is a great need for novel pharmaceuticals which have an advantageous therapeutic profile for the treatment of such diseases. The present invention is therefore based on the object of providing novel compounds which have an inhibitory effect on PARP.

The object is achieved by the tetrahydro-2H-isoquinolin-1-one derivatives according to the following general formula (I).

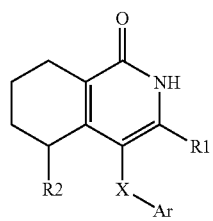

(I)

in which the meanings are:

X is a single bond, O, S, NH or $N(C_1-C_3$-alkyl);

R1 is hydrogen, fluorine, chlorine, —CN, methoxy, —OCF$_3$ or $C_1-C_3$-alkyl which is optionally substituted by hydroxy, chlorine, methoxy or one, two or three fluorine atoms;

R2 is hydrogen, fluorine, —CN, hydroxy, methoxy, —OCF$_3$, —NH$_2$, —NH($C_1-C_3$-alkyl), —N($C_1-C_3$-alkyl)$_2$ or $C_1-C_3$-alkyl which is optionally substituted by hydroxy, chlorine, methoxy or one, two or three fluorine atoms;

R3 is —(C$_1$-C$_3$-alkyl)-NR4R5, —SO$_2$NR4R5, —C(O) NR4R5, —C(H)=N—OR9, —NHC(O)R6, —(C$_1$-C$_3$-alkyl)-NHC(O)R6, —NHSO$_2$R6, —(C$_1$-C$_3$-alkyl)-NHSO$_2$R6 or —CH(OH)R7;

R4 and R5 are independently of one another selected from the group consisting of: hydrogen; unsubstituted or at least monosubstituted $C_1-C_{10}$-alkyl, $C_2-C_6$-alkenyl, $C_2-C_6$-alkynyl, aryl, heteroaryl and heterocyclyl, where the substituents are selected from the group consisting of: aryl, heteroaryl, heterocyclyl, —O-aryl, fluorine, chlorine, bromine, —CF$_3$, —OCF$_3$, —NO$_2$, —CN, —C(O)R8, —NHC(O)(C$_1$-C$_3$-alkyl), —NH$_2$, hydroxy, $C_1-C_6$-alkyl, $C_1-C_3$-alkoxy, —NH(C$_1$-C$_3$-alkyl), —N(C$_1$-C$_3$-alkyl)$_2$, —NH-aryl, —NH-heteroaryl, —NH—C(O)-heteroaryl, —SO$_2$NH$_2$, —SO$_2$(C$_1$-C$_3$-alkyl) and —NH—SO$_2$(C$_1$-C$_3$-alkyl), and the aryl, heteroaryl and heterocyclyl fragments of these substituents may in turn be at least monosubstituted by fluorine, chlorine, bromine, oxo, —CF$_3$, —OCF$_3$, —NO$_2$, —CN, aryl, heteroaryl, —NHC(O)(C$_1$-C$_3$-alkyl), —COOH, hydroxy, $C_1-C_3$-alkyl, $C_1-C_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or —N(C$_1$-C$_3$-alkyl)$_2$; or R4 and R5 form together with the nitrogen atom to which they are bonded unsubstituted or at least monosubstituted heterocyclyl, where the substituents are selected from the group consisting of: aryl, heteroaryl, heterocyclyl, oxo, fluorine, chlorine, bromine, —CF$_3$, —OCF$_3$, —NO$_2$, —CN, —C(O) R8, —NHC(O)(C$_1$-C$_3$-alkyl), —NH$_2$, hydroxy, $C_1-C_3$-alkyl, $C_1-C_3$-alkoxy, —NH(C$_1$-C$_3$-alkyl), —N(C$_1$-C$_3$-alkyl)$_2$, —SO$_2$NH$_2$, —SO$_2$(C$_1$-C$_3$-alkyl) and —NH—SO$_2$(C$_1$-C$_3$-alkyl), and, of these substituents, aryl, heterocyclyl and heteroaryl in turn may be at least monosubstituted by fluorine, chlorine, bromine, hydroxy, $C_1-C_3$-alkyl or $C_1-C_3$-alkoxy;

R6 is unsubstituted or at least monosubstituted $C_1-C_6$-alkyl, phenyl, heteroaryl or heterocyclyl, where the substituents are selected from the group consisting of:

fluorine, chlorine, bromine, aryl, heterocyclyl, heteroaryl, —CF$_3$, —OCF$_3$, —NO$_2$, —CN, —C(O)R8, —NHC(O)(C$_1$-C$_3$-alkyl), —NH$_2$, hydroxy, $C_1-C_3$-alkyl, $C_1-C_3$-alkoxy, —O-heteroaryl, —O-aryl, —NH(C$_1$-C$_3$-alkyl), —N(C$_1$-C$_3$-alkyl)$_2$, —SO$_2$NH$_2$, —SO$_2$(C$_1$-C$_3$-alkyl) and —NH—SO$_2$(C$_1$-C$_3$-alkyl), and the aryl, heterocyclyl and heteroaryl fragments of these substituents may in turn be at least monosubstituted by fluorine, chlorine, bromine, hydroxy, $C_1-C_3$-alkyl or $C_1-C_3$-alkoxy;

R7 is selected from the group consisting of:

hydrogen; unsubstituted or at least monosubstituted $C_1-C_6$-alkyl, phenyl and heteroaryl, where the substituents are selected from the group consisting of:

fluorine, chlorine, bromine, —CF$_3$, —OCF$_3$, —NO$_2$, —CN, —C(O)R8, —NHC(O)(C$_1$-C$_3$-alkyl), —NH$_2$, hydroxy, $C_1-C_3$-alkyl, $C_1-C_3$-alkoxy, —NH(C$_1$-C$_3$-alkyl), —N(C$_1$-C$_3$-alkyl)$_2$, —SO$_2$NH$_2$, —SO$_2$(C$_1$-C$_3$-alkyl) and —NH—SO$_2$(C$_1$-C$_3$-alkyl);

R8 is $C_1-C_3$-alkoxy, —O-phenyl, $C_1-C_3$-alkyl, —NH$_2$, —NH (C$_1$-C$_3$-alkyl), —N(C$_1$-C$_3$-alkyl)$_2$ or phenyl, and the above phenyl fragments may in turn be at least monosubstituted by fluorine, chlorine, bromine, oxo, —CF$_3$, —OCF$_3$, —NO$_2$, —CN, aryl, heteroaryl, —NHC(O)(C$_1$-C$_3$-alkyl), —COOH, hydroxy, C$_1$-C$_3$-alkyl, C$_1$-C$_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or —N(C$_1$-C$_3$-alkyl)$_2$;

R9 is selected from the group consisting of:
hydrogen; unsubstituted or at least monosubstituted C$_1$-C$_6$-alkyl and phenyl,
where the substituents are selected from the group consisting of:
fluorine, chlorine, bromine, aryl, heterocyclyl, heteroaryl, —CF$_3$, —OCF$_3$, —NO$_2$, —CN, —C(O)R8, —NHC(O)(C$_1$-C$_3$-alkyl), C$_1$-C$_3$-alkyl, C$_1$-C$_3$-alkoxy, —NH(C$_1$-C$_3$-alkyl), —N(C$_1$-C$_3$-alkyl)$_2$, —SO$_2$NH$_2$, —SO$_2$(C$_1$-C$_3$-alkyl) and —NH—SO$_2$(C$_1$-C$_3$-alkyl),
and, of these substituents, aryl, heterocyclyl and heteroaryl may in turn be at least monosubstituted by fluorine, chlorine, bromine, C$_1$-C$_3$-alkyl or C$_1$-C$_3$-alkoxy;

Ar is unsubstituted or at least monosubstituted aryl or heteroaryl, where the substituents are selected from the group consisting of: fluorine, chlorine, bromine, —CF$_3$, —OCF$_3$, —NO$_2$, —CN, —C(O)R8, —NH$_2$, —NHC(O)(C$_1$-C$_6$-alkyl), hydroxy, C$_1$-C$_6$-alkyl, C$_1$-C$_6$-alkoxy, —CH$_2$—CH$_2$—CH$_2$—, —CH$_2$—O—C(O)—, —CH$_2$—C(O)—O—, —CH$_2$—NH—C(O)—, —CH$_2$—N(CH$_3$)—C(O)—, —CH$_2$—C(O)—NH—, —NH(C$_1$-C$_6$-alkyl), —N(C$_1$-C$_6$-alkyl)$_2$, —SO$_2$(C$_1$-C$_6$-alkyl), heterocyclyl, heteroaryl, aryl and R3,
and, of these substituents, heterocyclyl, aryl and heteroaryl may in turn be at least monosubstituted by C$_1$-C$_6$-alkyl, C$_1$-C$_6$-alkoxy, fluorine, chlorine, bromine, trifluoromethyl, trifluoromethoxy or OH;

heteroaryl is a 5 to 10-membered, aromatic, mono- or bicyclic heterocycle which comprises one or more heteroatoms selected from N, O and S;

aryl is a 5 to 10-membered, aromatic, mono- or bicycle;

heterocyclyl is a 5 to 10-membered, non-aromatic, mono- or bicyclic heterocycle which comprises one or more heteroatoms selected from N, O and S;

or a physiologically tolerated salt thereof;

provided that Ar is not unsubstituted phenyl when X is a single bond.

The above meanings of the substituents R$^1$ to R$^8$, X, Ar, heteroaryl, heterocyclyl and aryl are the basic meanings (definitions) of the respective substituents.

DETAILED DESCRIPTION

The tetrahydro-2H-isoquinolin-1-one derivatives of the invention according to formula (I) differ in an advantageous manner from previously disclosed isoquinolin-1-one-based PARP inhibitors because, firstly, the second ring of the isoquinolinone basic structure is in hydrogenated form and, secondly, an aryl or heteroaryl substituent is present in position 4 on the isoquinolinone basic structure either directly or via the linker X. The majority of previously disclosed isoquinolin-1-one-based PARP inhibitors have (virtually) planar aromatic basic structures. Many of these planar PARP inhibitors may have DNA-binding or DNA-intercalating properties which are responsible for the suboptimal safety profile (cf. Southan et al., Current Medicinal Chemistry 2003, 10, 321-340). Since the isoquinolinone basic structure in the compounds of the invention is no longer planar in position 5, 6, 7 and 8 owing to its saturation, these molecules display an advantageous safety profile compared with the planar aromatic basic structures. The presence of an aryl or heteroaryl substituent in position 4 of the basic structure has an additional beneficial effect on the PARP-inhibitory effect of the compounds of the invention.

Where groups, fragments, radicals or substituents such as, for example, aryl, heteroaryl, alkyl, alkoxy etc. are present more than once in the compounds according to formula (I), they all have independently of one another the abovementioned meanings and may thus in each (individual) case have either an identical or a mutually independent meaning. The following statements apply to (for example) aryl and any other radical irrespective of its designation as aryl group, substituent, fragment or radical. A further example is the —N(C$_1$-C$_3$-alkyl)$_2$ group in which the two alkyl substituents may be either identical or different (for example twice ethyl or once propyl and once methyl).

Where a substituent, for example aryl, in the above definitions of compounds according to formula (I) may be unsubstituted or at least monosubstituted by a group of further substituents, for example C$_1$-C$_6$-alkyl, C$_1$-C$_6$-alkoxy, halogen etc., then the selection in those cases where aryl is polysubstituted takes place from the series of further substituents independently of one another. Thus, for example, when aryl is disubstituted, all combinations of the further substituents are included. Aryl may thus be for example disubstituted with ethyl, aryl may in each case be monosubstituted with methyl and ethoxy, aryl may in each case be monosubstituted with ethyl and fluorine, aryl may be disubstituted with methoxy, etc.

Alkyl radicals may be either linear or branched, acyclic or cyclic. This also applies when they are a part of another group such as, for example, alkoxy groups (C$_1$-C$_{10}$-alkyl-O—), alkoxycarbonyl groups or amino groups, or if they are substituted.

Examples of alkyl groups are: methyl, ethyl, propyl, butyl, pentyl, hexyl, heptyl, octyl, nonyl or decyl. Included therein are both the n isomers of these radicals and isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals, such as, for example, aryl, heteroaryl, alkoxy or halogen. It is moreover possible for the additional substituents to occur in any desired position of the alkyl radical. The term alkyl also includes cycloalkyl and cycloalkylalkyl (alkyl which is in turn substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. The ring systems may also, where appropriate, be polycyclic, such as decalinyl, norbornanyl, bornanyl or adamantanyl. The cycloalkyl radicals may be unsubstituted or optionally substituted by one or more further radicals as mentioned above by way of example for the alkyl radicals.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl. The term alkenyl here expressly also includes cycloalkenyl radicals and cycloalkenylalkyl radicals (alkyl which is substituted by cycloalkenyl) which comprise at least three carbon atoms. Examples of cycloalkenyl are: cyclopentenyl, cyclohexenyl, cycloheptenyl and cyclooctenyl.

The alkenyl radicals may have one to three conjugated or non-conjugated double bonds (that is to say also alk-dienyl and alk-trienyl radicals), preferably one double bond in a linear or branched chain, and the same applies to the triple bonds for alkynyl radicals. The alkenyl and alkynyl radicals may be unsubstituted or optionally substituted by one or more further radicals as mentioned above by way of example for the alkyl radicals.

Unless stated otherwise, the aforementioned aryl, heteroaryl and heterocyclyl radicals may either unsubstituted or have one or more, for example 1, 2, 3 or 4 further, of the aforementioned substituents in any desired position. For example, the substituent in monosubstituted phenyl radicals may be in position 2, 3 or 4, the substituents in disubstituted phenyl radicals may be in the 2,3 position, 2,4 position, 2,5 position, 2,6 position, 3,4 position or 3,5 position. The substituents in trisubstituted phenyl radicals may be in the 2,3,4 position, 2,3,5 position, 2,3,6 position, 2,4,5 position, 2,4,6 position or the 3,4,5 position. The substituents in tetrasubstituted phenyl radicals may be in the 2,3,4,5 position, the 2,3,4,6 position or in the 2,3,5,6 position.

The aforementioned and the following definitions relating to monovalent radicals apply in exactly the same way to divalent radicals such as phenylene, naphthylene or heteroarylene. These divalent radicals (fragments) may be linked to the adjacent groups for any desired ring carbon atom. In the case of phenylene radicals, this may be in the 1,2 position (ortho-phenylene), 1,3 position (meta-phenylene) or 1,4 position (para-phenylene). In the case of a 5-membered aromatic system comprising a heteroatom, such as, for example, thiophene or furan, the two free bonds may be in the 2,3 position, 2,4 position, 2,5 position or 3,4 position. A divalent radical derived from a 6-membered aromatic system having a heteroatom, such as, for example, pyridine, may be a 2,3-, 2,4-, 2,5-, 2,6-, 3,4- or 3,5-pyridinediyl radical. In the case of nonsymmetrical divalent radicals, the present invention also includes all positional isomers, i.e. in the case of, for example, a 2,3-pyridinediyl radical the compound in which one adjacent group is located in position 2 and the other adjacent group is located in position 3 is included just as much as the compound in which one adjacent group is located in position 3 and the other adjacent group is located in position 2.

Unless stated otherwise, heteroaryl radicals heteroarylene radicals, heterocyclyl radicals and heterocyclylene radicals, and rings which are formed by two groups bonded to nitrogen, are preferably derived from completely saturated, partly or wholly unsaturated heterocycles (i.e. heterocycloalkanes, heterocycloalkenes, heteroaromatics) which comprise 1, 2, 3 or 4 heteroatoms which may be either different or identical. They are preferably derived from heterocycles which comprise 1, 2 or 3, particularly preferably 1 or 2, heteroatoms which may be identical or different. Unless stated otherwise, the heterocycles are mono- or polycyclic, for example monocyclic, bicyclic or tricyclic. They are preferably monocyclic or bicyclic. 5-Membered, 6-membered or 7-membered rings are preferred, and 5-membered or 6-membered rings are particularly preferred. In the case of polycyclic heterocycles having 2 and more heteroatoms, these may occur all in the same ring or be distributed over a plurality of rings.

Radicals referred to as heteroaryl in the present invention are derived from monocyclic or bicyclic aromatic heterocycles. Examples of heteroaryl are: pyrrolyl, furanyl (=furyl), thiophenyl (=thienyl), imidazolyl, pyrazolyl, 1,2,3-triazolyl, 1,2,4-triazolyl, 1,3-oxazolyl (=Oxazolyl), 1,2-oxazolyl (=isoxazolyl), oxadiazolyl, 1,3-thiazolyl (=thiazolyl), 1,2-thiazolyl (=isothiazolyl), tetrazolyl, pyridinyl (=pyridyl), pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, quinolinyl, isoquinolinyl, quinazolinyl, quinoxalinyl, phthalazinyl, thienothiophenyl, 1,8-naphthyridinyl, other naphthyridinyls, pteridinyl or thiazolo[3,2-b][1,2,4]-triazolyl. Where the systems are non-monocyclic, also included for the second ring for each of the abovementioned heteroaryls is the saturated form (perhydro form) or the partly unsaturated form (for example the dihydro form or tetrahydro form) or the maximally unsaturated (non-aromatic) form, as long as the respective forms are known and stable. The term heteroaryl thus includes in the present invention for example also bicyclic radicals in which either both rings are aromatic or bicyclic radicals in which only one ring is aromatic. Such examples of heteroaryl are: 3H-indolinyl, 2(1H)-quinolinonyl, 4-oxo-1,4-dihydroquinolinyl, 2H-1-oxoisoquinolyl, 1,2-dihydroquinolinyl, 3,4-dihydroquinolinyl, 1,2-dihydroisoquinolinyl, 3,4-dihydroisoquinolinyl, chromonyl, chromanyl, 1,3-benzodioxolyl, oxindolyl, 1,2,3,4-tetrahydroisoquinolinyl, 5,6-dihydroquinolinyl, 5,6-dihydroisoquinolyl, 5,6,7,8-tetrahydroquinolinyl or 5,6,7,8-tetrahydroisoquinolyl.

Radicals referred to as heterocyclyl in the present invention are derived from monocyclic or bicyclic nonaromatic heterocycles. Nonaromatic heterocycles mean hereinafter in particular heterocycloalkanes (completely saturated heterocycles) and heterocycloalkenes (partly unsaturated heterocycles). In the case of the heterocycloalkenes, also included are compounds having two or more double bonds, which may optionally also be conjugated together. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl, 1,3-dioxolanyl, 1,4-dioxinyl, pyranyl, thiopyranyl, tetrahydro-1,2-oxazinyl, tetrahydro-1,3-oxazinyl, morpholinyl, thiomorpholinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, azepanyl, 2-oxoazepanyl, 1,2,3,4-tetrahydropyridinyl, 1,2-dihydropyridinyl, 1,4-dihydropyridinyl, 1,2,3,6-tetrahydropyridinyl, 4(3H)-pyrimidonyl, 1,4,5,6-tetrahydropyrimidinyl, 2-pyrrolinyl, 3-pyrrolinyl, 2-imidazolinyl, 2-pyrazolinyl, 3,4-dihydro-2H-pyranyl, dihydrofuranyl, 7-oxabicyclo[2.2.1]heptenyl, dihydrothiophenyl and dihydrothiopyranyl. The degree of saturation of heterocyclic groups is indicated in the respective definition.

Substituents derived from these heterocycles may be linked via any suitable carbon atom, and be provided with further substituents. Radicals derived from nitrogen-containing heterocycles may have a hydrogen atom or another substituent on the corresponding nitrogen atom. Examples include pyrrole, imidazole, pyrrolidine, morpholine, piperazine radicals etc. These nitrogen-containing heterocyclic radicals may also be linked via the ring nitrogen atom, especially if the corresponding heterocyclic radical is linked to a carbon atom. For example, a thienyl radical may be in the form of 2-thienyl or 3-thienyl, a piperidinyl radical in the form of 1-piperidinyl (piperidino), 2-piperidinyl, 3-piperidinyl or 4-piperidinyl. Suitable nitrogen-containing heterocycles may also be in the form of N-oxides or of quaternary salts which have a counter ion which is derived from a physiologically acceptable acid. For example, pyridinyl radicals may be in the form of pyridine N-oxides. Suitable sulfur-containing heterocycles may also be in the form of S-oxide or S—S-dioxide.

Radicals referred to as aryl in the present invention are derived from monocyclic or bicyclic aromatic systems which comprise no ring heteroatoms. Where the systems are non-monocyclic, also for the second ring in the term aryl is the saturated form (perhydro form) or the partly unsaturated form (for example the dihydro form or tetrahydro form), as long as the respective forms are known and stable. The term aryl also includes in the present invention for example bicyclic radicals in which either both rings are aromatic or bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl.

Arylalkyl (such as aryl-($C_1$-$C_6$-alkyl)-) means that an alkyl radical (such as $C_1$-$C_6$-alkyl) is in turn substituted by an aryl radical. Heteroarylalkyl (such as heteroaryl-($C_1$-$C_6$-alkyl)-) means that an alkyl radical (such as $C_1$-$C_6$-alkyl) is in turn substituted by a heteroaryl radical. Heterocyclylalkyl (such as heterocyclyl-($C_1$-$C_6$-alkyl)-) means that an alkyl radical (such as $C_1$-$C_6$-alkyl) is in turn substituted by a heterocyclyl radical. Reference is made to the foregoing definitions for the definitions and possible substitutions of alkyl, heteroaryl, heterocyclyl and aryl.

Where bivalent substituents in which the two free valences are not located on the (carbon) atom are defined in the present invention, such as, for example, —$CH_2$—$CH_2$—$CH_2$— (propylene) or —$CH_2$—O—C(O)— in the case of Ar, this means that this bivalent substituent is linked with both free valences to the same radical (for example Ar) and thus brings about the formation of a (further) ring. The bivalent substituent is usually linked to different atoms of the corresponding radical, but may where appropriate—if this is possible—also be linked by the two free valences to the same atom of the radical.

Halogen is fluorine, chlorine, bromine or iodine, is preferably fluorine, chlorine or bromine, and is particularly preferably fluorine or chlorine.

The present invention includes all stereoisomeric forms of compounds according to formula (I). Asymmetric carbon atoms in compounds according to formula (I) may have independently of one another S configurations or R configurations. The invention includes all possible enantiomers and diastereomers and mixtures of two or more stereoisomers, for example mixtures of enantiomers and/or diastereomers, in all amounts and ratios. It is thus possible for compounds of the present invention which exist as enantiomers to be in enantiopure form, both as dextrorotatory and levorotatory antipodes, in the form of racemates and in the form of mixtures of the two enantiomers in all ratios. In the case of cis/trans isomers, the invention includes both the cis form and the trans form, and mixtures of these forms in all ratios. The present invention relates to all these forms. Preparation of the individual stereoisomers is possible if desired by separating a mixture by conventional methods, for example by chromatography or crystallization, through the use of stereochemically pure starting materials for the synthesis or by stereoselective synthesis. It is also possible alternatively to carry out a derivatization before separating the stereoisomers. Separation of a mixture of stereoisomers can be carried out with the compounds of the formula (I) or with the appropriate intermediates during the synthesis. The present invention further includes also all tautomeric forms of compounds according to formula (I), in particular keto/enol tautomerism, i.e. the corresponding compounds may be either in their keto form or in their enol form or in mixtures thereof in all the ratios.

Where the compounds according to formula (I) comprise one or more acidic or basic groups, the present invention also includes the correspondingly physiologically or toxicologically acceptable salts.

Physiologically acceptable salts are, because their solubility in water is greater than that of the starting or basic compounds, particularly suitable for medical applications. These salts must have a physiologically acceptable anion or cation. Suitable physiologically acceptable acid addition salts of the compounds of the invention are salts of inorganic acids such as hydrochloric acid, hydrobromic, phosphoric, metaphosphoric, nitric, sulfonic and sulfuric acids, and organic acids such as, for example, acetic acid, theophyllineacetic acid, methylenebis-b-oxynaphthonic, benzenesulfonic, benzoic, citric, ethanesulfonic, salicylic, fumaric, gluconic, glycolic, isethionic, lactic, lactobionic, maleic, malic, methanesulfonic, succinic, p-toluenesulfonic, tartaric and trifluoroacetic acids. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the framework of the invention as useful intermediates for preparing or purifying pharmaceutically acceptable salts and/or for use in non-therapeutic, for example in vitro, applications.

Where compounds of the formula (I) comprise both acidic and basic groups in the same molecule, the present invention includes—in addition to the salt forms detailed previously—also inner salts or betaines (zwitterions).

The corresponding salts of the compounds according to formula (I) can be obtained by conventional methods which are known to the skilled worker, for example by reacting with an organic or inorganic acid or base in a solvent or dispersant, or by anion or cation exchange with other salts.

The present invention additionally includes all solvates of compounds according to formula (I), for example hydrates or adducts with alcohol, active metabolites of compounds according to formula (I), and derivatives which comprise a physiologically acceptable group which can be eliminated, for example esters or amides.

The term "physiologically functional derivative" used herein refers to any physiologically acceptable derivative of a compound of the invention of the formula I, e.g. an ester which, on administration to a mammal such as, for example, a human, is able (directly or indirectly) to form a compound of the formula I or an active metabolite thereof.

Physiologically functional derivatives also include prodrugs of the compounds of the invention. Such prodrugs may be metabolized in vivo to a compound of the invention. These prodrugs may themselves be active or not and the present invention likewise relates to them.

The compounds of the invention may also exist in various polymorphous forms, e.g. as amorphous and crystalline polymorphous forms. All polymorphous forms of the compounds of the invention belong within the framework of the invention and are a further aspect of the invention.

Preferred compounds of the general formula (I) are those compounds in which one, more than one or all of the aforementioned substituents $R^1$ to $R^8$, X, Ar, heteroaryl, heterocyclyl and aryl have independently of one another the meanings (definitions) detailed below, and the present invention relates to all possible combinations of preferred, more preferred, much more preferred, even much more preferred and particularly preferred meanings (definitions), likewise in combination with the substituents in their basic meaning.

X is preferably a single bond, NH or N($C_1$-$C_3$-alkyl);

X is particularly preferably a single bond or NH;

R1 is preferably hydrogen or $C_1$-$C_3$-alkyl which is optionally substituted by hydroxy, chlorine, methoxy or one, two or three fluorine atoms;

R1 is particularly preferably hydrogen or $C_1$-$C_3$-alkyl;

R2 is preferably hydrogen, fluorine, —OCF$_3$, hydroxy, methoxy, —NH$_2$ or C$_1$-C$_3$-alkyl;

R2 is particularly preferably hydrogen;

Ar is preferably unsubstituted or at least monosubstituted phenyl or heteroaryl,
  where the substituents are selected from the group consisting of: fluorine, chlorine, —CF$_3$, —OCF$_3$, C(O)(C$_1$-C$_3$-alkyl), —NH$_2$, —NHC(O)(C$_1$-C$_3$-alkyl), hydroxy, C$_1$-C$_3$-alkyl, C$_1$-C$_3$-alkoxy, —CH$_2$—CH$_2$—CH$_2$—, —CH$_2$—O—C(O)—, —CH$_2$—C(O)—O—, —CH$_2$—NH—C(O)—, —CH$_2$—N(CH$_3$)—C(O)—, —CH$_2$—C(O)—NH—, —NH(C$_1$-C$_3$-alkyl), —N(C$_1$-C$_3$-alkyl)$_2$, —SO$_2$(C$_1$-C$_3$-alkyl), heterocyclyl, heteroaryl, aryl and R3,
  and, of these substituents, heterocyclyl and heteroaryl in turn may be at least monosubstituted by C$_1$-C$_3$-alkyl, C$_1$-C$_3$-alkoxy, fluorine, chlorine, bromine, trifluoromethyl, trifluoromethoxy or OH;

Ar is more preferably unsubstituted or at least monosubstituted phenyl, thienyl, furanyl or pyridinyl,
  where the substituents are selected from the group consisting of:
  fluorine, chlorine, —CF$_3$, —OCF$_3$, C(O)(C$_1$-C$_3$-alkyl), —NH$_2$, —NHC(O)(C$_1$-C$_3$-alkyl), hydroxy, C$_1$-C$_3$-alkyl, C$_1$-C$_3$-alkoxy, —CH$_2$—CH$_2$—CH$_2$—, —CH$_2$—O—C(O)—, —CH$_2$—C(O)—O—, —CH$_2$—NH—C(O)—, —CH$_2$—N(CH$_3$)—C(O)—, —CH$_2$—C(O)—NH—, —NH(C$_1$-C$_3$-alkyl), —N(C$_1$-C$_3$-alkyl)$_2$, —SO$_2$(C$_1$-C$_3$-alkyl) and R3;

Ar is much more preferably monosubstituted phenyl, thienyl, furanyl or pyridinyl,
  where the substituent is selected from the group consisting of:
  fluorine, chlorine, —CF$_3$, —OCF$_3$, C(O)(C$_1$-C$_3$-alkyl), —NH$_2$, —NHC(O)(C$_1$-C$_3$-alkyl), hydroxy, C$_1$-C$_3$-alkyl, C$_1$-C$_3$-alkoxy, —NH(C$_1$-C$_3$-alkyl), —N(C$_1$-C$_3$-alkyl)$_2$, —SO$_2$(C$_1$-C$_3$-alkyl) and R3;
  and the substituent and X are in the meta position relative to one another; this is to be understood to mean that the fragment Ar of the compound according to formula (I)—with the above definitions of Ar—is substituted by one substituent, and Ar is in turn substituted by X in the position meta to this substituent. The meta substitution does not depend on the position of the heteroatom of Ar.

Ar is even much more preferably monosubstituted phenyl, thienyl, furanyl or pyridinyl,
  where the substituent is selected from the group consisting of:
  fluorine, chlorine, —OCF$_3$, —C(O)CH$_3$, —NHC(O)CH$_3$, hydroxy, —N(CH$_3$)$_2$, ethoxy, —SO$_2$CH$_3$ and R3;
  and the substituent and X are in the meta position relative to one another;

Ar is particularly preferably furanyl monosubstituted by R3, and R3 and X are in the meta position relative to one another.

R3 is preferably —CH$_2$—NR4R5, —SO$_2$NR4R5, —C(O)NR4R5, —CH$_2$NHC(O)R6, —CH$_2$—NHSO$_2$R6 or —CH(OH)R7;

R3 is more preferably —CH$_2$—NR4R5, —C(O)NR4R5, —CH$_2$—NHC(O)R6, CH$_2$—NHSO$_2$R6 or —CH(OH)R7;

R3 is much more preferably —CH$_2$—NR4R5, —C(O)NR4R5 or —CH(OH)R7;

R3 is particularly preferably —CH$_2$—NR4R5;

R4 and R5 are independently of one another preferably selected from the group consisting of: hydrogen; unsubstituted or at least monosubstituted C$_1$-C$_{10}$-alkyl, C$_2$-C$_6$-alkenyl, phenyl, indanyl, heterocyclyl and heteroaryl, where the substituents are selected from the group consisting of: phenyl, heteroaryl, heterocyclyl, —O-phenyl, fluorine, —CN, —C(O)NH$_2$, —C(O)(C$_1$-C$_3$-alkyl), —C(O)-phenyl, —N(C$_1$-C$_3$-alkyl), —C(O)-phenyl, —N(C$_1$-C$_3$-alkyl)$_2$, —NH(C$_1$-C$_3$-alkyl), —NH$_2$, —NH-heteroaryl, —NH—C(O)-heteroaryl, C$_1$-C$_6$-alkyl, C$_1$-C$_3$-alkoxy and hydroxy,
  and the phenyl, heterocyclyl and heteroaryl fragments of these substituents may in turn be at least monosubstituted by fluorine, chlorine, bromine, oxo, —CF$_3$, —OCF$_3$, —NO$_2$, —CN, phenyl, pyridinyl, —NHC(O)(C$_1$-C$_3$-alkyl), —COOH, hydroxy, C$_1$-C$_3$-alkyl, C$_1$-C$_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or N(C$_1$-C$_3$-alkyl)$_2$; or R4 and R5 form together with the nitrogen atom to which they are bonded unsubstituted or at least monosubstituted heterocyclyl,
  where the substituents are selected from the group consisting of: phenyl, heteroaryl, heterocyclyl, oxo, fluorine, chlorine, —C(O)(C$_1$-C$_3$-alkyl), —C(O)-phenyl and hydroxy,
  and the phenyl, heterocyclyl and heteroaryl fragments of these substituents may in turn be at least monosubstituted by fluorine or C$_1$-C$_3$-alkyl;

R4 is more preferably selected from the group consisting of: hydrogen, unsubstituted or at least monosubstituted C$_1$-C$_{10}$-alkyl, C$_2$-C$_6$-alkenyl, phenyl, indanyl, heterocyclyl and heteroaryl,
  where the substituents are selected form the group consisting of: phenyl, heteroaryl, heterocyclyl, —O-phenyl, fluorine, —CN, —C(O)NH$_2$, —C(O)(C$_1$-C$_3$-alkyl), —C(O)-phenyl, —N(C$_1$-C$_3$-alkyl)$_2$, —NH(C$_1$-C$_3$-alkyl), —NH$_2$, —NH-heteroaryl, —NH—C(O)-heteroaryl, C$_1$-C$_6$-alkyl, C$_1$-C$_3$-alkoxy and hydroxy,
  and the phenyl, heterocyclyl and heteroaryl fragments of these substituents may in turn by fluorine, chlorine, bromine, oxo, —CF$_3$, —OCF$_3$, —NO$_2$, —CN, phenyl, pyridinyl, —NHC(O)(C$_1$-C$_3$-alkyl), —COOH, hydroxy, C$_1$-C$_3$-alkyl, C$_1$-C$_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or —N(C$_1$-C$_3$-alkyl)$_2$; and R5 is hydrogen; or R4 and R5 form together with the nitrogen atom to which they are bonded unsubstituted or at least monosubstituted heterocyclyl,
  where the substituents are selected from the group consisting of: phenyl, heteroaryl, heterocyclyl, oxo, fluorine, chlorine, —C(O)(C$_1$-C$_3$-alkyl), —C(O)-phenyl and hydroxy,
  and the phenyl, heterocyclyl and heteroaryl fragments of these substituents may in turn be at least monosubstituted by fluorine or C$_1$-C$_3$-alkyl;

R4 is much more preferably selected from the group consisting of; hydrogen; unsubstituted or at least monosubstituted C$_1$-C$_{10}$-alkyl, cyclohexenyl, indanyl, phenyl, pyrrolidinyl, pyrrolyl, pyrazolyl, furanyl and piperidinyl,
  where the substituents are selected from the group consisting of: fluorine, —CN, —C(O)NH$_2$, —O-phenyl, —C(O)-phenyl, —N(CH$_3$)$_2$, C$_1$-C$_3$-alkyl, C$_1$-C$_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, of which the substituents are in turn selected from the group consisting of: fluorine, chlorine, oxo, $CF_3$, —$OCF_3$, —$NO_2$, phenyl, pyridinyl, —$NHC(O)CH_3$, —COOH, hydroxy, $C_1$-$C_3$-alkyl, $C_1$-$C_3$-alkoxy, —$SO_2NH_2$, —$C(O)NH_2$ and —$NH(CH_3)_2$; and R5 is hydrogen; or R4 and R5 form together with the nitrogen atom to which they are bonded a radical selected from the group consisting of: unsubstituted or at least monosubstituted piperidinyl, pyrrolidinyl, morpholinyl and piperazinyl, where the substituents are selected from the group consisting of: fluorine, —$C(O)(C_1$-$C_3$-alkyl), oxo, $C_1$-$C_3$-alkyl, hydroxy, unsubstituted or at least monosubstituted phenyl, imidazolyl, pyridinyl, pyrimidinyl, piperidinyl and pyrrolidinyl, the substituents of which are in turn fluorine or $C_1$-$C_3$-alkyl;

R4 is particularly preferably unsubstituted or at least monosubstituted $C_1$-$C_6$-alkyl, where the substituents are selected from the group consisting of: —$N(CH_3)_2$, hydroxy, unsubstituted or at least monosubstituted phenyl, pyridinyl, imidazolyl, indolyl, benzimidazolyl, pyrazolyl and pyrrolidinyl, the substituents of which are in turn selected from the group consisting of: —$NHC(O)CH_3$, $C_1$-$C_3$-alkyl, $C_1$-$C_3$-alkoxy, —$SO_2NH_2$ and —$C(O)NH_2$; and R5 is hydrogen; or R4 and R5 form together with the nitrogen atom to which they are bonded a radical selected from the group consisting of: unsubstituted or at least monosubstituted pyrrolidinyl, piperidinyl and piperazinyl, where the substituents are selected from the group consisting of: $C_1$-$C_3$-alkyl, hydroxy and pyrrolidinyl;

R6 is preferably unsubstituted or at least monosubstituted $C_1$-$C_6$-alkyl, phenyl or heteroaryl, where the substituents are selected from the group consisting of: fluorine, chlorine, bromine, —$CF_3$, —$OCF_3$, —$NHC(O)(C_1$-$C_3$-alkyl), hydroxy, $C_1$-$C_3$-alkyl, $C_1$-$C_3$-alkoxy, —O-heteroaryl, phenyl, —$NH_2$, —$NH(C_1$-$C_3$-alkyl), —$N(C_1$-$C_3$-alkyl)$_2$ and heterocyclyl, and the phenyl, heteroaryl and heterocyclyl fragments of these substituents may in turn be at least monosubstituted by fluorine, chlorine, bromine, hydroxy, $C_1$-$C_3$-alkyl or $C_1$-$C_3$-alkoxy;

R6 is more preferably —$CF_3$ or unsubstituted or at least monosubstituted $C_1$-$C_6$-alkyl, pyridinyl, furanyl or phenyl, where the substituents are selected from the group consisting of: fluorine, —$NHC(O)(C_1$-$C_3$-alkyl), hydroxy, $C_1$-$C_3$-alkyl, $C_1$-$C_3$-alkoxy and —O-pyridinyl;

R6 is particularly preferably $C_1$-$C_6$-alkyl, pyridinyl, —$CF_3$, furanyl or phenyl, and phenyl may optionally be substituted by —$NH(O)CH_3$, —O-pyridinyl or methoxy;

R7 is preferably selected from the group consisting of:
hydrogen; unsubstituted or at least monosubstituted $C_1$-$C_6$-alkyl, phenyl and pyridinyl, where the substituents are selected from the group consisting of: fluorine, chlorine, bromine, hydroxy, $C_1$-$C_3$-alkyl and $C_1$-$C_3$-alkoxy;

R7 is particularly preferably hydrogen;
R9 is preferably hydrogen or pyrrolidinylethyl;
aryl is preferably phenyl, indanyl or naphthyl;
aryl is more preferably phenyl or indanyl;
aryl is particularly preferably phenyl;
heteroaryl is preferably pyridinyl, thienyl, pyrimidinyl, imidazolyl, furanyl, indolyl, benzimidazolyl, pyrazolyl, 1,3-benzodioxolyl, triazolyl, thiazolyl, isoxazolyl, pyrrolyl, pyrazinyl, oxazolyl, pyridazinyl, quinolinyl, isoquinolyl, benzofuranyl, 3-oxo-1,3-dihydroisobenzofuranyl or 4,5,6,7-tetrahydrobenzothiazolyl;

heteroaryl is more preferably pyridinyl, thienyl, pyrimidinyl, imidazolyl, furanyl, benzimidazolyl, pyrazolyl, thiazolyl, isoxazolyl, pyrrolyl, pyrazinyl, 3-oxo-1,3-dihydroisobenzofuranyl or 4,5,6,7-tetrahydrobenzothiazolyl heteroaryl is particularly preferably pyridinyl, thienyl, pyrazolyl, furanyl or benzimidazolyl;

heterocyclyl is preferably morpholinyl, pyrrolidinyl, piperidinyl, tetrahydropyranyl, thiazolidinyl, dihydroisoxazolyl, piperazinyl or tetrahydrofuranyl;

heterocyclyl is particularly preferably morpholinyl, pyrrolidinyl, piperidinyl or piperazinyl;

examples of embodiments with preferred compounds of the general formula (I) with reference to the meanings (definitions) described above are:

i) R1 to R7, X, Ar, heteroaryl and heterocyclyl each have their preferred meaning; or ii) R1 has its preferred meaning and all other substituents have their basic meaning; or iii) R2 has its preferred meaning and all other substituents have their basic meaning; or iv) R3 has its preferred meaning and R1, R2, R4 to R8, X, Ar, heteroaryl, heterocyclyl and aryl have their basic meaning; or v) R4 and R5 each have their preferred meaning and all other substituents have their basic meaning; or vi) R6 has its preferred meaning and all other substituents have their basic meaning; or vii) R7 has its preferred meaning and all other substituents have their basic meaning; or viii) R9 has its preferred meaning and all other substituents have their basic meaning; or ix) X has its preferred meaning and all other substituents have their basic meaning; or x) Ar has its preferred meaning and all other substituents have their basic meaning; or xi) aryl has its preferred meaning and all other substituents have their basic meaning; or xii) heteroaryl has its preferred meaning and all other substituents have their basic meaning; or xiii) heterocyclyl has its preferred meaning and all other substituents have their basic meaning; or xiv) aryl, heterocyclyl and heteroaryl each have their preferred meaning and all other substituents have their basic meaning; or xv) R4 to R7 and R9 each have their preferred meaning and all other substituents have their basic meaning; or xvi) R6 and Ar each have their more preferred meaning and R1 to R5, R7, X, heteroaryl and heterocyclyl each have their preferred meaning; or xvii) R1 and 2 each have their particularly preferred meaning, Ar has its much more preferred meaning, R3, R4, R6 and heteroaryl each have their more preferred meaning and R7, X and heterocyclyl each have their preferred meaning; or xviii) R1, R2, R7 and X each have their particularly preferred meaning and R3, R4 and Ar each have their much more preferred meaning; or xix) R1 to R4 and X each have their particularly preferred meaning and Ar has its even much more preferred meaning; or xx) R1 to R4, X and Ar each have their particularly preferred meaning; or xxi) R1 to R3, X and Ar each have their particularly preferred meaning and R4 has its much more preferred meaning; or xxii) R1, R2 and X each have their preferred meaning, R4 has its more preferred meaning, Ar has its even much more preferred meaning and R3, heteroaryl and heterocyclyl each have their particularly preferred meaning; or xxiii) R1, R2, X, heteroaryl and heterocyclyl each have their particularly preferred meaning, R4 and Ar each have their more preferred meaning, R3 has its much more preferred meaning and R7 has its preferred meaning; or xxiv) R1, R2 and R7 each have their particularly preferred meaning, R3 has its much more preferred meaning, R4, R6, Ar and heteroaryl each have their more preferred meaning and X and heterocyclyl each have their preferred meaning; or xxv) R1, R2 and Ar each have their particularly preferred meaning, R3, R7, X and heterocyclyl each have their preferred meaning and R4, R6 and heteroaryl each have their more preferred meaning; or xxvi) R1, R2, R4, R5, R7, X, heteroaryl and heterocyclyl each have their preferred meaning, Ar has its much more preferred meaning, R6 has its more preferred meaning and R3 and R9 have their basic meaning; or xxvii) R1, R2, X, Ar, heteroaryl and heterocyclyl each have their preferred meaning, R3, R4 and R6 each have their more preferred meaning and R7 has its particularly preferred meaning; or xxviii) R1 to R7, X, heteroaryl, heterocyclyl and aryl each have their preferred meaning and Ar has its basic meaning; or xxix) R1, R2, X, heteroaryl, heterocyclyl and aryl each have their preferred meaning, R3, R4 and R6 each have their more preferred meaning, R7 has its particularly preferred meaning and Ar has its basic meaning; or xxx) R1, R2, R4 to R7, R9, X, heteroaryl and heterocyclyl each have their preferred meaning, Ar has its more preferred meaning and R3 has its basic meaning; or xxxi) R1, R2, R9, X, heteroaryl and heterocyclyl each have their preferred meaning, R4, R6 and Ar each have their more preferred meaning, R7 has its particularly preferred meaning and R3 has its basic meaning; or xxxii) R3 to R7, Ar, heteroaryl and heterocyclyl each have their preferred meaning and R1, R2 and X each have their basic meaning; or xxxiii) Ar has its much more preferred meaning, X, aryl, heteroaryl and heterocyclyl each have their preferred meaning and all other substituents have their basic meaning; or xxxiv) X, aryl, heteroaryl and heterocyclyl each have their preferred meaning, R3, R4 and R6 each have their more preferred meaning, R7 has its particularly preferred meaning and R1, R2 and Ar each have their basic meaning.

As stated above, the preferred compounds of the general formula (I) are not confined to the aforementioned examples. On the contrary, all combinations of the individual substituents in their basic meaning with the preferred, more preferred, much more preferred, even much more preferred or particularly preferred meanings of the other substituents or all combinations of the preferred, more preferred, much more preferred, even much more preferred or particularly preferred meanings of the individual substituents which are not detailed above as example are also an aspect of this invention. This of course applies only as far as the definitions of the respective substituents permits such a combination.

Most preferred compounds according to the general formula (I) are selected from the group consisting of:

4-(3-methanesulfonylphenylamino)-3-methyl-5,6,7,8-tetrahydro-2H-isoquinolin-1-one, 4-(3-acetylphenylamino)-3-methyl-5,6,7,8-tetrahydro-2H-isoquinolin-1-one, 4-(5-butylaminomethylfuran-2-yl)-3-methyl-5,6,7,8-tetrahydro-2H-isoquinolin-1-one, 3-methyl-4-(5-pyrrolidin-1-ylmethylfuran-2-yl)-5,6,7,8-tetrahydro-2H-isoquinolin-1-one, 4-[5-(3-hydroxypyrrolidin-1-ylmethyl)furan-2-yl]-5,6,7,8-tetrahydro-2H-isoquinolin-1-one, 4-(5-{[(4-pyrrolidin-1-ylpiperidin-1-ylmethyl)amino]methyl}furan-2-yl)-5, 6,7,8-tetrahydro-2H-isoquinolin-1-one, 4-{5-[(2-dimethylaminoethylamino)methyl]furan-2-yl)-5,6,7,8-tetrahydro-2H-isoquinolin-1-one, 4-{5-[(2-hydroxy-2-phenylethylamino)methyl]furan-2-yl}-5,6,7,8-tetrahydro-2H-isoquinolin-1-one, 4-(5-{[(4-methylpiperazin-1-ylmethyl)amino]methyl}furan-2-yl)-5,6,7,8-tetrahydro-2H-isoquinolin-1-one, 4-(5-{[(1-methyl-1H-pyrazol-4-ylmethyl)amino]methyl}furan-2-yl)-5,6,7,8-tetrahydro-2H-isoquinolin-1-one, 4-(5-butylaminomethylfuran-2-yl)-5,6,7,8-tetrahydro-2H-isoquinolin-1-one and 4-(5-hydroxymethylfuran-2-yl)-3-methyl-5,6,7,8-tetrahydro-2H-isoquinolin-1-one.

The compounds of the formula I can be prepared by various chemical methods which likewise belong to the present invention. Some typical routes are outlined in the reaction sequences referred to below as schemes 1 to 3. Substituents R are in each case defined as indicated above unless indicated otherwise hereinafter. The starting compounds and the intermediate compounds (intermediates) are either commercially available or can be prepared by methods known to the skilled worker.

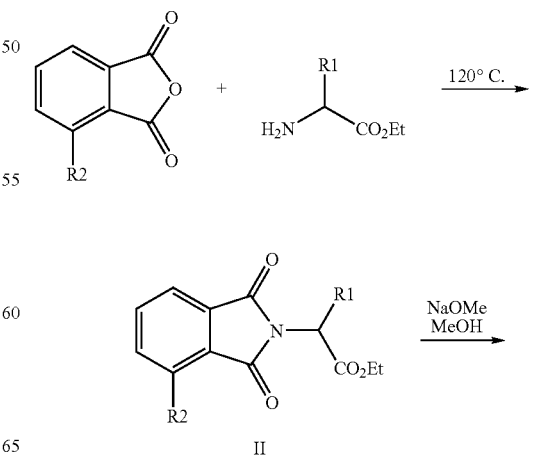

Scheme 1

-continued

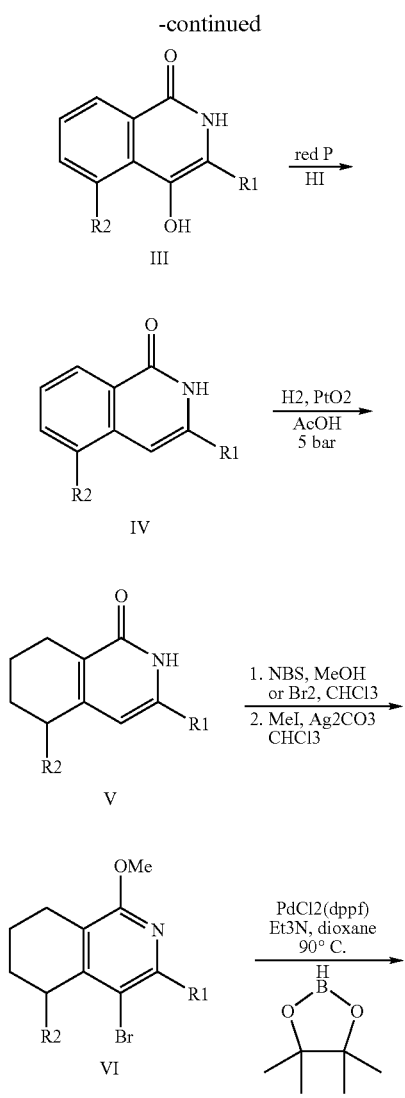

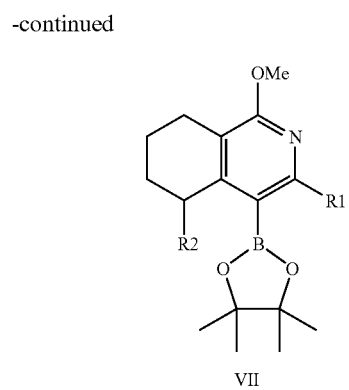

Intermediate II can be obtained by heating phthalic anhydride with amino acid esters. Subsequent treatment of the phthalimides II with sodium methanolate in methanol under reflux affords intermediates III which are converted after reductive dehydroxylation with red phosphorus in hydroiodic acid into the isoquinolinones IV. Partial hydrogenation of these intermediates, some of which are also commercially available (e.g. for R1=H) or can be prepared by another route, affords the tetrahydroisoquinolinones V. Intermediate VI can be prepared therefrom by bromination (which can be carried out for example with N-bromosuccinimide in methanol or with bromine in chloroform as solvent) and subsequent O-alkylation (e.g. by methyl iodide in chloroform with the addition of silver carbonate). Intermediate VII can be prepared from the halide VI by palladium-catalyzed borylation (e.g. by reaction with 4,4,5,5-tetramethyl-1,3,2-dioxaborolane with palladium dichloride 1,1'-bis(diphenylphosphino)ferrocene as catalyst and triethylamine as base in 1,4-dioxane as solvent). Both intermediates VI and VII are suitable for further reaction to give the compounds I (see schemes 2 and 3). The radical R2 can where appropriate be modified during or following any reaction step in schemes 1 to 3 by means known to the skilled worker.

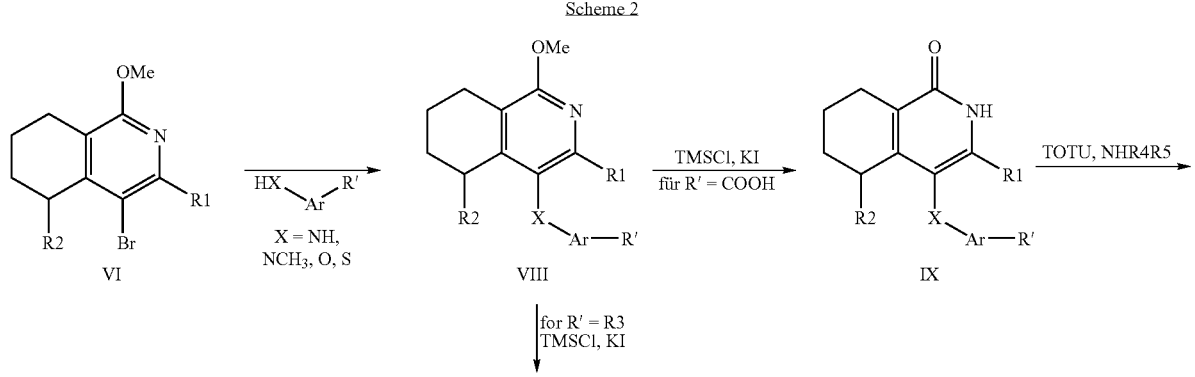

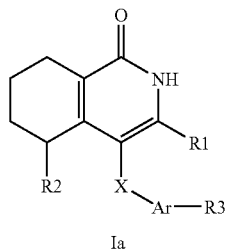

Ia

Compounds of the formula VIII with X equal to NH or N(C$_1$-C$_3$-alkyl) can be prepared by Hartwig-Buchwald amination with aromatic amines catalyzed by palladium (for example with palladium dibenzylideneacetone and bis(tert-butyl)biphenylphosphine as catalyst and sodium tert-butanolate or potassium tert-butanolate as base in toluene). Compounds of the formula VIII with X=O, S can be prepared by reacting sodium or potassium phenolates, or sodium or potassium thiophenolates, with copper catalysis (for example copper(I) chloride, copper(I) oxide or copper powder in high-boiling solvents such as DMF or collidine). Elimination of the methyl group from the compounds of the formula VIII (e.g. by trimethylchlorosilane and potassium iodide in acetonitrile) affords compounds of the formula Ia. (scheme 2). It is possible in this case for the heteroaryl/aryl fragment (Ar) to be either unsubstituted (R'=H) or at least monosubstituted, where the substituents may be those listed in the basic meaning of Ar (such as R'=R$^3$ or heteroaryl) or else R'=COOH. When suitable functional groups are present, for example when R' is a carboxylate function, further compounds of the formula Ia in which R3 is —C(O)NR4R5 can be prepared by forming an amide linkage with coupling reagents such as O-[(ethoxycarbonyl)-cyanomethyleneamino]-N,N,N',N'-tetramethyluronium tetrafluoroborate (TOTU).

Compounds of the formula X can be prepared by palladium-catalyzed Suzuki coupling of an aromatic boronic acid or of a boronic ester and of the intermediates VI (scheme 3). Preparation of compounds of the formula X may also start from intermediate VII which is coupled by palladium-catalyzed Suzuki coupling (e.g. with palladium dichloride 1,1'-bis(diphenylphosphino)ferrocene as catalyst and potassium carbonate as base in dimethylformamide) with aromatic halides (e.g. Br—Ar—R"; R" may in this case be for example hydrogen, —CHO or —COOH) (scheme 3).

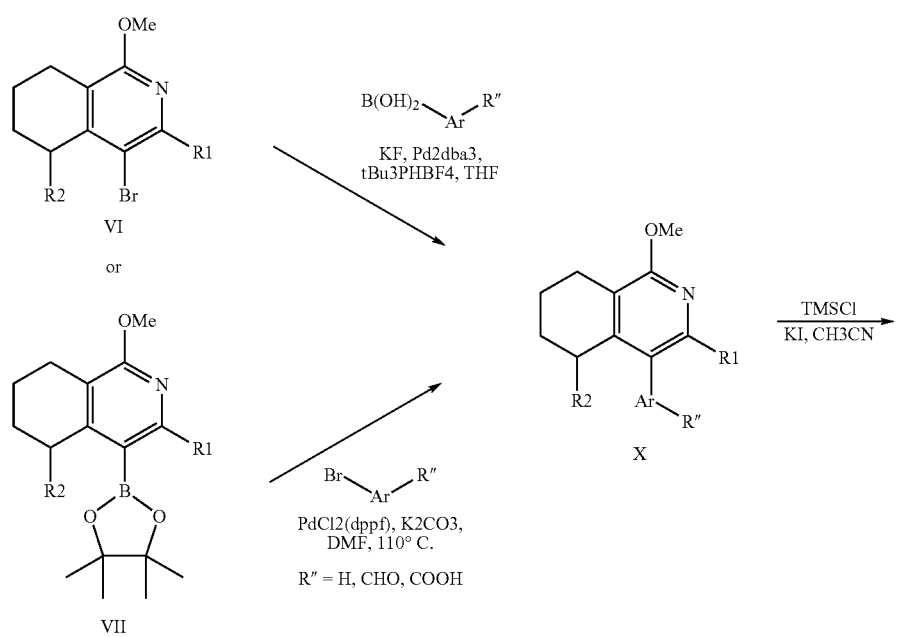

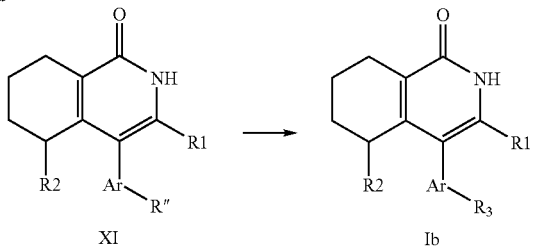

for R" CHO
NaCNBH$_3$, or MP triacetoxyborohydride, HNR4R5
or
NaBH$_4$
or
1. NaCNBH$_3$, NH$_4$OAc. 2. R6COCl or R6SO2Cl, pyridine
for R"=COOH
HNR(3)R(4), TFFH or PPA Elimination of the methyl group from the compounds of the formula X (e.g. by trimethylchlorosilane and potassium iodide in acetonitrile) affords tetrahydroisoquinolinones of the formula Xi. Compounds of the formula Ib in which R3 is —CH2NR4R5 are prepared by employing compounds Xi with R"=—CHO, which are reacted by reductive amination with amines NR4R5. It is possible in this case to use reducing agents such as sodium cyanoborohydride or solid phase-bound triacetoxyborohydride.

Compounds of the formula Ib in which R3 is —CH$_2$OH are prepared by employing compounds XI with R"=—CHO, which are reacted by reduction for example with sodium borohydride.

Compounds of the formula Ib in which R3 is —CH$_2$NHC(O)R6 or —CH$_2$NHSO$_2$R6 are prepared by firstly carrying out a reductive amination with ammonium acetate, and coupling the aminomethyl compounds obtained in this way with appropriate acid chlorides or acids or with sulfonyl chlorides.

Compounds of the formula Ib in which R3 is —C(O)NR4R5 are prepared by employing compounds of the formula Xi with R"=—COOH, which are coupled with amines HNR4R5. It is possible in this case to use various suitable condensing agents such as carbodiimides, TFFH or phosphonic anhydrides (e.g. PPA).

Compounds of the formula Ib in which R3 is —CHNOR9 are prepared by employing compounds XI with R"=—CHO, which are reacted to form oximes with hydroxylamines R9ONH$_2$.

Compounds of the formula Ib in which R3 is —SO$_2$NR4R5 are prepared by employing compounds XI with R"=H, which are converted by chlorosulfonation (for example with chlorosulfonic acid and phosphorus pentachloride in chloroform) into the corresponding sulfochlorides, and the latter are then reacted with amines HNR4R5.

Compounds of the formula Ib in which R3 is —C(O)R6 are prepared by employing compounds Xi with R"=H, which are lithiated and then reacted with Weinreb amides R5C(O)NMe(OMe) to give the desired compounds.

Compounds of the formula Ib in which R3 is —CH(OH)R7 are prepared by lithiating compounds Xi with R"=H and then reacting with aldehydes R7CHO.

Compounds of the formula Ib in which R3 is —NHSO$_2$R6 are prepared by employing compounds XI with R"=—NH$_2$, which are reacted with sulfonyl chlorides R6SO$_2$Cl in the presence of a base.

Compounds of the formula Ib in which R3 is —NHC(O)R6 are prepared by employing compounds of the formula XI with R"=—NH$_2$, which are reacted with a suitable acid chloride in the presence of a base or with a suitable acid in the presence of a condensing agent.

Compounds of the formula Ib in which R3 is —(C$_2$-C$_3$-alkyl)-NR4R5 are prepared by employing compounds XI with R"=—CHO, which are reacted with a suitable Wittig reagent, with subsequent removal of protective groups and reductive amination of the aldehyde resulting therefrom with a suitable amine. The Wittig reagent is preferably Ph$_3$P=CHOR.

Compounds of the formula Ib in which R3 is —(C$_2$-C$_3$-alkyl)-NHC(O)R6 or —(C$_2$-C$_3$-alkyl)-NHSO$_2$R6 are prepared by employing compounds Xi with R"=—CHO, which are reacted with a suitable Wittig reagent, with subsequent removal of the protective groups and reductive amination of the aldehyde with ammonium acetate to give the amine. This amine is reacted with a suitable acid chloride R6C(O)Cl or with a suitable sulfonyl chloride R6SO$_2$Cl in the presence of a base to give the above-mentioned compounds.

It may be appropriate in all procedures for functional groups in the molecule to be protected temporarily in certain reaction protocols. Such protective groups are familiar to the skilled worker. Selection of a protective group for groups which come into consideration, and the methods for their introduction and elimination, are described in the literature and can be adapted where appropriate to the individual case without difficulties.

The present invention also relates to the use of compounds according to general formula (I) as pharmaceutical or medicament. Concerning the definitions of the substituents X, Ar, R$^1$ and R$^2$ (and of the other substituents defined via the aforementioned substituents), reference is made to the statements concerning the compounds as such.

The use of compounds according to general formula (I) as pharmaceuticals, where one, more than one or all of the aforementioned substituents have the preferred, more preferred, much more preferred, even much more preferred or particularly preferred meaning mentioned above, including all combinations with one another, is likewise an aspect of the present invention.

The compounds of the general formula (I) are PARP inhibitors and are accordingly suitable for the treatment of diseases which are related to PARP, are promoted thereby or result from its involvement.

Examples of diseases which can be treated with the compounds according to the present invention include: tissue damage resulting from cell damage or cell death owing to necrosis or apoptosis, neuronally mediated tissue damage or disorders, cerebral ischemia, head trauma, stroke, reperfusion damage, neurological disturbances and neurodegenerative disorders, vascular stroke, cardiovascular disorders, myocardial infarction, myocardial ischemia, experimental allergic encephalomyelitis (EAE), multiple sclerosis (MS), ischemia related to heart surgery, age-related macular degeneration, arthritis, arteriosclerosis, cancer, degenerative disorders of the skeletal muscles with subsequent replicative senescence, diabetes and diabetic myocardial disorders.

The compounds of the present invention are preferably employed for the treatment of diseases which are caused by ischemia or reperfusion damage. Diseases which can be treated are more preferably selected from the group consisting of: cerebral ischemia, reperfusion damage, cardiovascular disorders, myocardial infarction, myocardial ischemia and ischemia related to heart surgery.

The compounds of the present invention can be used in particular for the treatment of a myocardial infarction.

The term treatment in the above statements also includes the prophylaxis, therapy or cure of the aforementioned diseases.

All references to "compound(s) according to formula (I)" hereinafter refer to compound(s) of the formula (I) as described above, and their salts, solvates and physiologically functional derivatives as described herein.

The compounds according to formula (I) can be administered to animals and humans, preferably mammals and humans, particularly preferably humans. The compounds according to formula (I) can in this connection be administered themselves as pharmaceutical, in mixtures with one another or in mixtures with other pharmaceuticals or in the form of pharmaceutical compositions. Consequently, the use of compounds according to formula (I) for producing one or more medicaments for the prophylaxis and/or treatment of the aforementioned diseases, pharmaceutical compositions comprising an effective amount of at least one compound according to formula (I), and pharmaceutical compositions comprising an effective amount of at least one compound according to formula (I) for the prophylaxis and/or treatment of the aforementioned diseases are likewise aspects of the present invention.

The amount of a compound according to formula (I) which is necessary in order to achieve the desired biological effect depends on a number of factors, e.g. the specific compound chosen, the intended use, the mode of administration and the clinical condition of the patient. The daily dose is generally in the range from 0.3 mg to 100 mg (typically from 3 mg to 50 mg) per day per kilogram of body weight, e.g. 3-10 mg/kg/day. An intravenous dose may be for example in the range from 0.3 mg to 1.0 mg/kg, which can suitably be administered as infusion of from 10 ng to 100 ng per kilogram per minute. Suitable infusion solutions for these purposes may comprise for example from 0.1 ng to 10 mg, typically from 1 ng to 10 mg, per milliliter.

Single doses may comprise for example from 1 mg to 10 g of the active ingredient. Thus, ampules for injections may comprise for example from 1 mg to 100 mg, and single-dose formulations which can be administered orally, such as, for example, tablets or capsules, may comprise for example from 1.0 to 1000 mg, typically from 10 to 600 mg. In the case of pharmaceutically acceptable salts, the aforementioned weight data refer to the weight of the free compound from which the salt is derived. For the prophylaxis or therapy of the abovementioned conditions it is possible for the compounds of the formula (I) to be used themselves as compound, but they are preferably present together with an acceptable carrier in the form of a pharmaceutical composition. The carrier must, of course, be acceptable in the sense that it is compatible with the other ingredients of the composition and is not harmful for the patient's health (physiologically acceptable).

The carrier may be a solid or a liquid or both and is preferably formulated with the compound as single dose, for example as tablet which may comprise from 0.05% to 95% by weight of the active ingredient. Further pharmaceutically active substances may likewise be present, including further compounds of the formula (I). The pharmaceutical compositions of the invention can be produced by one of the known pharmaceutical methods, which essentially consist of mixing the ingredients with pharmacologically acceptable carriers and/or excipients.

Besides at least one compound according to formula (I) and one or more carriers, the pharmaceutical compositions of the invention may also comprise excipients. Examples of suitable excipients or additives are: fillers, binders, lubricants, wetting agents, stabilizers, emulsifiers, dispersants, preservatives, sweeteners, colorants, flavorings, aromatizing substances, thickeners, diluents, buffer substances, solvents, solubilizers, agents with which a depot effect can be achieved, salts to alter the osmotic pressure, coating agents or antioxidants.

The pharmaceutical compositions of the invention may for example be in the form of a pill, tablet, coated tablet, suckable tablet, granules, capsule, hard or soft gelatin capsule, aqueous solution, alcoholic solution, oily solution, syrup, emulsion, suspension, suppository, pastille, solution for injection or infusion, ointment, tincture, cream, lotion, dusting powder, spray, transdermal therapeutic system, nasal spray, aerosol, aerosol mixture, microcapsule, implant, rod or patch.

Pharmaceutical compositions of the invention are those suitable for oral, rectal, topical, peroral (for example sublingual) and parenteral (e.g. subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound according to formula (I); in the form of powders (gelatin capsules or sachets) or granules; as solution or suspension in an aqueous or non-aqueous liquid; or in the form of an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, lubricant, inert diluent and/or one (or more) surface-active/dispersing agent(s) in a suitable machine. Molded tablets can be produced by molding the compound, which is in powder form and is moistened with an inert liquid diluent, in a suitable machine. Examples of suitable diluents are starch, cellulose, sucrose, lactose or silica gel. The pharmaceutical compositions of the invention may additionally comprise substances which are not diluents, for example one or more lubricants such as magnesium stearate or talc, a colorant, a coating (coated tablets) or a lacquer.

Pharmaceutical compositions which are suitable for peroral (sublingual) administration comprise suckable tablets which contain a compound according to formula (I) with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound according to formula (I), which are preferably isotonic with the blood of the intended recipient. These preparations are preferably administered intravenously, although administration can also take place by subcutaneous, intramuscular or intradermal injection. These preparations can preferably be produced by mixing the compound with water, and making the resulting solution sterile and isotonic with blood. Injectable compositions of the invention generally comprise from 0.1 to 5% by weight of the active compound.

The sterile compositions for parenteral administration may preferably be aqueous or nonaqueous solutions, suspensions or emulsions. Solvents or vehicles which can be used are water, propylene glycol, polyethylene glycol and vegetable oils, especially olive oil, organic esters for injection, for example ethyl oleate, or other suitable organic solvents. These compositions may also comprise adjuvants, especially wetting agents, agents for adjusting isotonicity, emulsifiers, dispersants and stabilizers. Sterilization can take place in several ways, for example by aseptic filtration, by introducing sterilizing agents into the composition, by irradiation or by heating. The compositions may also be produced in the form of sterile solid compositions which on use are dissolved in sterile water or another sterile injection medium.

Pharmaceutical compositions suitable for rectal administration are preferably in the form of single-dose suppositories. These can be produced by mixing a compound according to formula (I) with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an optionally buffered aqueous solution, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described for example in Pharmaceutical Research, 2(6): 318 (1986).

The invention further relates to intermediates of compounds according to general formula (I). Intermediates according to general formula (XI) obtainable by the methods described above are also an aspect of the present invention. The intermediates (XI) are important especially when the linker X in compounds of the formula (I) is a single bond, and the substituent Ar is at least monosubstituted by R3.

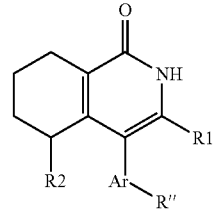

(XI)

where
R1 is hydrogen, fluorine, chlorine, —CN, methoxy, —OCF$_3$ or C$_1$-C$_3$-alkyl which is optionally substituted by hydroxy, chlorine, methoxy or one, two or three fluorine atoms;
R2 is hydrogen, fluorine, —CN, hydroxy, methoxy, —OCF$_3$, —NH$_2$, —NH(C$_1$-C$_3$-alkyl), —N(C$_1$-C$_3$-alkyl)$_2$ or C$_1$-C$_3$-alkyl which is optionally substituted by hydroxy, chlorine, methoxy or one, two or three fluorine atoms;
R8 is C$_1$-C$_3$-alkoxy, —O-phenyl, C$_1$-C$_3$-alkyl, —NH$_2$, —NH(C$_1$-C$_3$-alkyl), —N(C$_1$-C$_3$-alkyl)$_2$ or phenyl,
and the above phenyl fragments may in turn be at least monosubstituted by fluorine, chlorine, bromine, oxo, —CF$_3$, —OCF$_3$, —NO$_2$, —CN, aryl, heteroaryl, —NHC(O)(C$_1$-C$_3$-alkyl), —COOH, hydroxy, C$_1$-C$_3$-alkyl, C$_1$-C$_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or —N(C$_1$-C$_3$-alkyl)$_2$;
Ar is aryl or heteroaryl,
where this aryl or heteroaryl is optionally substituted by at least one substituent are selected from the group consisting of: fluorine, chlorine, bromine, —CF$_3$, —OCF$_3$, —NO$_2$, —CN, —C(O)R8, —NH$_2$, —NHC(O)(C$_1$-C$_6$-alkyl), hydroxy, C$_1$-C$_6$-alkyl, C$_1$-C$_6$-alkoxy, —CH$_2$—CH$_2$—CH$_2$, —CH$_2$—O—C(O)—, —CH$_2$—C(O)—O—, —CH$_2$—NH—C(O)—, —CH$_2$—N(CH$_3$)—C(O)—, —CH$_2$C(O)—NH—, —NH(C$_1$-C$_6$-alkyl), —N(C$_1$-C$_6$-alkyl)$_2$, —SO$_2$(C$_1$-C$_6$-alkyl), heterocyclyl, heteroaryl and aryl,
and, of these substituents, heterocyclyl, aryl and heteroaryl may in turn be at least monosubstituted by C$_1$-C$_6$-alkyl, C$_1$-C$_6$-alkoxy, fluorine, chlorine, bromine, trifluoromethyl, trifluoromethoxy or OH;
R" is —COOH, —CHO or —SO$_2$Cl;
heteroaryl is a 5 to 10-membered, aromatic, mono- or bicyclic heterocycle which comprises one or more heteroatoms selected from N, O and S;
heterocyclyl is a 5 to 10-membered, nonaromatic, mono- or bicyclic heterocycle which comprises one or more heteroatoms selected from N, O and S;
aryl is a 5 to 10-membered, aromatic mono- or bicycle.
Preferred compounds of the formula (XI) are those in which:
R1 is hydrogen or C$_1$-C$_3$-alkyl;
R2 is hydrogen;
Ar is phenyl, thienyl, furanyl or pyridinyl,
where this phenyl, thienyl, furanyl or pyridinyl is optionally substituted by at least one substituent are selected from the group consisting of: fluorine, chlorine, —CF$_3$, —OCF$_3$, —C(O)(C$_1$-C$_3$-alkyl), —NH$_2$, —NHC(O)(C$_1$-C$_3$-alkyl), hydroxy, C$_1$-C$_3$-alkyl, C$_1$-C$_3$-alkoxy, —CH$_2$—CH$_2$—CH$_2$—, —CH$_2$—O—C(O)—, —CH$_2$—C(O)—O—, —CH$_2$NH—C(O)—, —CH$_2$N(CH$_3$)—C(O)—, —CH$_2$—C(O)—NH—, —NH(C$_1$-C$_3$-alkyl), —N(C$_1$-C$_3$-alkyl)$_2$ and —SO$_2$(C$_1$-C$_3$-alkyl);

R" is —COOH, —CHO or —SO$_2$Cl;

Particularly preferred compounds of the formula (XI) are those in which

R1 is hydrogen or C$_1$-C$_3$-alkyl;

R2 is hydrogen;

Ar is phenyl, furanyl, thienyl or pyridinyl, where R" and the tetrahydroquinolinone fragment are in the meta position relative to one another;

R" is —CHO or —COOH.

Experimental Section

| List of abbreviations | |
|---|---|
| $^t$Bu | tert-butyl |
| dba | dibenzylideneacetone |
| DCM | dichloromethane |
| DMAP | 4-dimethylaminopyridine |
| DMF | N,N-dimethylformamide |
| D6-DMSO | deuterated dimethyl sulfoxide |
| eq. | mole equivalent |
| MP | highly crosslinked macroporous polystyrene |
| NBS | N-bromosuccinimide |
| PdCl$_2$(dppf) | 1,1'-bis(diphenylphosphino)ferrocenepalladium(II) chloride |
| PPA | propanephosphonic anhydride |
| RF | reflux |
| RT | room temperature |
| RP-HPLC | reverse phase high performance chromatography |
| SCX | cation exchanger ('strong cation exchanger') |
| TFFH | tetramethylfluoroaminidinium hexafluorophosphate |
| TFA | trifluoroacetic acid |
| TFH | tetrahydrofuran |
| TMS | trimethylsilyl |
| TOTU | O-[(ethoxycarbonyl)cyanomethyleneamino]-N,N,N',N'-tetramethyluronium tetrafluoroborate |

Synthesis of the Phthalimides of the Formula II

The synthesis according to scheme 1 is demonstrated by means of compound 1:

Ethyl 2-(1,3-dioxo-1,3-dihydroisoindol-2-yl)propionate (Compound 1)

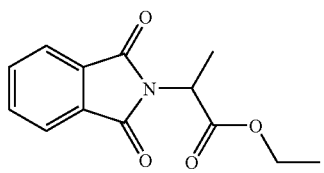

20.87 g (0.141 mol) of phthalic anhydride together with 16.5 g (0.141 mol) of ethyl aminopropionate in an open round-bottom flask at 120° C. for 5 h. 300 ml of cyclohexane are added, and the mixture is heated to reflux. The hot cyclohexane solution is decanted off from the remaining oil and completely concentrated. A slowly solidifying viscous oil is obtained (31 g, 89% yield).

MS: m/z=248 (M+1)

1H-NMR (CDCl3): δ=7.87 (2H, m); 7.74 (2H, m); 4.96 (1H, q, J=7.3 Hz); 4.21 (2H, m); 1.70 (3H, d, J=7.3 Hz); 1.24 (3H, t, J=7.1 Hz).

4-Hydroxy-3-methyl-2H-isoquinolin-1-one (Compound 2)

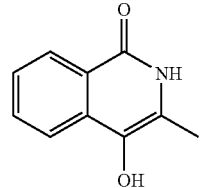

31.8 g (129 mmol) of compound 1 are dissolved in 22 ml of absolute methanol and, after addition of 15.2 ml of 28% sodium methanolate solution (257 mmol), heated to reflux for 3 h. The solution is concentrated and conc. aqueous ammonia solution is added to the residue. After 2 h, the solid is filtered off with suction and washed with cold water. 14.1 g (63% yield) of white solid are obtained.

MS: m/z=176 (M+1)

1H-NMR (CD3OD): δ=8.21 (1H, d, J=8.8 Hz); 8.14 (1H, d, J=8.3 Hz); 7.65 (1H, m); 7.38 (1H, m); 2.30 (3H, s).

3-Methyl-2H-isoquinolin-1-one (Compound 3)

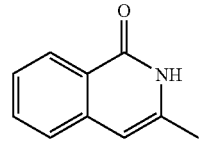

24.6 g (140 mmol) of 4-hydroxy-3-methyl-2H-isoquinolin-1-one are heated together with 9.13 g (294 mmol) of red phosphorus in 55% hydriodic acid (130 ml) at 160° C. for 7 days. The cooled mixture is poured into water and extracted with dichloromethane. 10.2 g (46% yield) of a white solid are obtained.

MS: m/z=160 (M+1)

1H-NMR (CDCl23): δ 10.55 (1H, s); 8.37 (1H, d, J=8.1 Hz); 7.62 (1H, m); 7.43 (2H, m); 6.31 (1H, s); 2.37 (3H, s).

3-Methyl-5,6,7,8-tetrahydro-2H-isoquinolin-1-one (Compound 4)

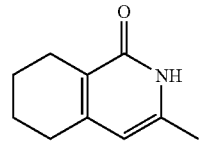

8.45 g (53 mmol) of 3-methyl-2H-isoquinolin-1-one are dissolved in 80 ml of glacial acetic acid and, after addition of 168 mg (0.74 mmol) of platinum(IV) oxide, hydrogenated under 5 bar at RT for 8 h. The suspension is filtered and concentrated and the residue is recrystallized from methanol. 7.15 g (83%) of a colorless oil are obtained.

MS: m/z=164 (M+1)
1H-NMR (CDCl3): δ 10.7 (1H, s); 5.78 (1H, s); 2.50 (4H, m); 2.22 (3H, s); 1.73 (4H, m).

5,6,7,8-Tetrahydro-2H-isoquinolin-1-one (compound 5)

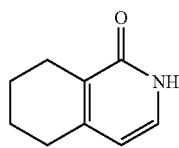

60 g (413 mmol) of 2H-isoquinolin-1-one (=isocarbostyril) are dissolved in 1 l of glacial acetic acid and, after addition of 2.3 g (10 mmol) of platinum(IV) oxide, hydrogenated under 3 bar at RT until conversion is complete. This entailed changing the catalyst after 3 days and a further 5 days. The suspension is filtered, concentrated and again concentrated after addition of toluene. The crude product is recrystallized from 1.6 l of water. Long needles are filtered off, and the mother liquor is concentrated and dried and separated on silica gel. 36.8 g (60%) of a colorless oil are obtained.

MS: m/z=150 (M+1)
1H-NMR (D6-DMSO): δ=11.20 (1H, s); 7.08 (1H, d, J=6.8 Hz); 5.90 (1H, d, J=6.8 Hz); 2.47 (2H, m); 2.30 (2H, m); 1.64 (4H, m).

4-Bromo-3-methyl-5,6,7,8-tetrahydro-2H-isoquinolin-1-one (Compound 6)

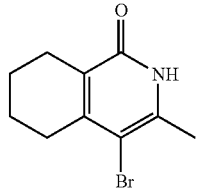

7.15 g (43.8 mmol) of compound 4 are dissolved in 50 ml of methanol at 0° C., and a total of 7.4 g (41.6 mmol) of N-bromosuccinimide is added in portions. After a reaction time of 3 h at 0°, the residue from filtration with suction is washed with a little cold water and dichloromethane. 8.9 g (84% yield) of the colorless bromide are obtained.

MS: m/z=242/244 (M+1)
1H-NMR (CDCl3): δ=12.4 (1H, s); 2.57 (4H, m); 2.43 (3H, s); 1.75 (4H, m).

4-Bromo-5,6,7,8-tetrahydro-2H-isoquinolin-1-one (Compound 7)

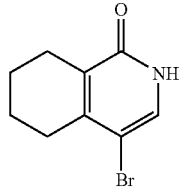

32.4 g (217 mmol) of tetrahydroisoquinolinone (compound 5) is dissolved in 300 ml of chloroform at 5° C. and then 11.2 ml (34.7 g, 217 mmol) of bromine, dissolved in 150 ml of chloroform, are added dropwise over the course of 1 h. The mixture is stirred while cooling in ice for a further hour and then neutralized with 150 ml of saturated NaHCO3 solution and filtered with suction. The organic phase of the filtrate is extracted with dichloromethane and concentrated. The residue is mixed with ethyl acetate, filtered off with suction and dried together with the first residue in a vacuum drying oven at 45° C. 47.7 g (96%) of colorless bromide are obtained.

MS: m/z=228/230 (M+1)
1H-NMR (CDCl3): δ=9.50 (1H, s); 8.03 (1H, s); 2.28 (2H, m); 2.18 (2H, m); 1.85 (4H, m).

4-Bromo-1-methoxy-3-methyl-5,6,7,8-tetrahydroisoquinoline (Compound 8)

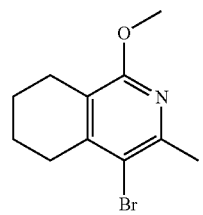

8.9 g (36.8 mmol) of 4-bromo-3-methyl-5,6,7,8-tetrahydro-2H-isoquinolin-1-one are dissolved in 200 ml of chloroform and, after addition of 13.7 g (49.6 mmol) of silver(I) carbonate and 16.2 ml (36.5 g, 257 mmol) of methyl iodide, stirred at 50° C. for 3 h. After a further 24 h at RT, the suspension is filtered through Celite, concentrated and chromatographed on silica gel using n-heptane with addition of 2% ethyl acetate. A colorless oil (7.8 g, 83% yield) is obtained.

MS: m/z=256/258 (M+1)
1H-NMR (CDCl3): δ=3.89 (3H, s), 2.65 (2H, m); 2.53 (2H, m); 2.51 (3H, s); 1.75 (4H, m).

4-Bromo-1-methoxy-5,6,7,8-tetrahydroisoquinoline (Compound 9)

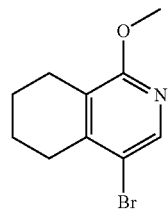

47.7 g (209 mmol) of 4-bromo-5,6,7,8-tetrahydro-2H-isoquinolin-1-one are dissolved in 1 l of chloroform and, after addition of 77.8 g (282 mmol) of silver(I) carbonate and 53.5 ml (118.7 g, 836 mmol) of methyl iodide, stirred at 50° C. for 3 h. After cooling, the suspension is filtered through Celite, concentrated and chromatographed on silica gel using n-heptane with addition of 2% ethyl acetate. A colorless oil (42.5 g, 84% yield) is obtained.

MS: m/z=242/244 (M+1)
1H-NMR (CDCl3): δ=8.03 (1H, s); 3.90 (3H, s); 2.66 (2H, m); 2.57 (2H, m); 1.78 (4H, m).

1-Methoxy-3-methyl-4-(4,4,5,5-tetramethyl-[1,3,2]dioxaborolan-2-yl)-5, 6,7,8-tetrahydroisoquinoline (Compound 10)

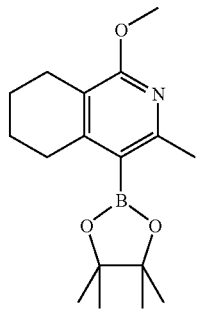

128 mg (0.5 mmol) of the bromide 8, 218 µl (1.64 mmol) of triethylamine and 83 mg (0.65 mmol) of 4,4,5,5-tetramethyl-1,3,2-dioxaborolane are dissolved in 2 ml of dioxane under argon, finally 19 mg (0.027 mmol) of PdCl2(dppf) are added, and the mixture is stirred at 90° C. for 60 h and then for a further 2.5 h at 150° C. in a microwave. The mixture is diluted with water and ethyl acetate, and the organic phase is washed with water, concentrated and purified on silica gel. A white solid (100 mg, 66% yield) is obtained.

MS: m/z=304 (M+1)
1H-NMR (CDCl3): δ=4.08 (3H, s); 2.68 (2H, m); 2.58 (3H, s); 2.52 (2H, m); 1.75 (4H, m); 1.38 (12H, s).

1-Methoxy-4-(4,4,5,5-tetramethyl-[1,3,2]dioxaborolan-2-yl)-5,6,7,8-tetrahydroisoquinoline (Compound 11)

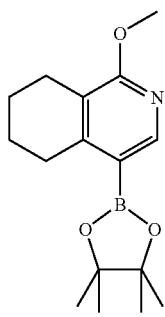

8.0 g (33 mol) of the bromide 9, 14.4 ml (109 mmol) of triethylamine and 5.5 g (42.9 mmol) of 4,4,5,5-tetramethyl-1,3,2-dioxaborolane are dissolved in 50 ml of dioxane under argon, finally 1.28 g (1.75 mmol) of PdCl2(dppf) are added, and the mixture is stirred at 90° C. for 18 h. The cooled mixture is mixed with water and extracted twice with ethyl acetate, and the organic phase is dried, concentrated and chromatographed on silica gel. A white solid (7.75 g, 81% yield) is obtained.

MS: m/z=290 (M+1)
1H-NMR (CDCl3): δ=8.01 (1H, s); 4.07 (3H, s); 2.66 (2H, m); 2.51 (2H, m); 1.75 (4H, m); 1.38 (12H, s).

Hartwig-Buchwald aminations of bromides of the formula VI to give compounds of the formula VIII.

General Procedure;

1 eq. of bromide (compound 8 or 9), 1.5 eq. of aniline and 1.4 eq. of NaOtBu are introduced into absolute toluene (2 ml/mmol) under argon. After stirring at RT for 10 min, 0.05 eq. of tris(dibenzylideneacetone)-dipalladium and 0.2 eq. of di-tert-butylphosphinobiphenyl are added, and the mixture is reacted at 150° C. in a microwave (CEM Discover) for 60 min. The reaction mixture is diluted with water and ethyl acetate, and the organic phase is separated off, concentrated and purified by RP-HPLC. Basic compounds are isolated as trifluoroacetates.

Ethyl 3-(1-methoxy-5,6,7,8-tetrahydroisoquinolin-4-ylamino)benzoate (Compound 12)

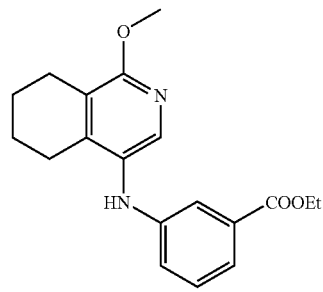

580 mg (4.9 mmol) of 95% pure KO$^t$Bu are introduced into 20 ml of abs. toluene. After evacuation and ventilation with argon three times, 847 mg (3.5 mmol) of 4-bromo-1-methoxy-5,6,7,8-tetrahydroisoquinoline, and 868 mg (5.25 mmol) of ethyl 3-aminobenzoate are added. Addition of 160 mg (0.175 mmol) of tris(dibenzylidene)dipalladium and 209 mg (0.7 mmol) of di-tert-butylphosphinobiphenyl is followed by heating at 100° C. for three hours. For workup, the mixture is concentrated and the residue is partitioned between H$_2$O and ethyl acetate. The phases are separated and the aqueous phase is extracted three times more. The combined organic phases are washed once more with H$_2$O, dried with Na$_2$SO$_4$ and concentrated. Further purification takes place by chromatography on silica gel (CH$_2$Cl$_2$/MeOH 99:1), resulting in 640 mg of the title compound. Yield: 55%.

The following further compounds are prepared in accordance with the general procedure:

| Compound | Name | |
|---|---|---|
| 13 | 3-(1-methoxy-5,6,7,8-tetrahydroisoquinolin-4-ylamino)phenol | 271 (M + 1) |
| 14 | 3-(1-methoxy-5,6,7,8-tetrahydroisoquinolin-4-ylamino)-N-methylbenzamide | 312 (M + 1) |
| 15 | (1-methoxy-5,6,7,8-tetrahydroisoquinolin-4-yl)(4-pyridin-4-ylthiazol-2-yl)amine | 339 (M + 1) |

-continued

| Compound | Name | |
|---|---|---|
| 16 | (1-methoxy-5,6,7,8-tetrahydroisoquinolin-4-yl)(3,4,5,6-tetrahydro-2H-[1,2']bipyridinyl-5'-yl)amine | 339 (M + 1) |
| 17 | N-[3-(1-methoxy-5,6,7,8-tetrahydroisoquinolin-4-ylamino)phenyl]acetamide | 312 (M + 1) |
| 18 | (3-methanesulfonylphenyl)(1-methoxy-5,6,7,8-tetrahydroisoquinolin-4-yl)amine | 333 (M + 1) |
| 19 | (3-methanesulfonylphenyl)(1-methoxy-3-methyl-5,6,7,8-tetrahydroisoquinolin-4-yl)amine | 337 (M + 1) |
| 20 | [3-(1-methoxy-5,6,7,8-tetrahydroisoquinolin-4-ylamino)phenyl]methanol | 285 (M + 1) |
| 21 | (6-methoxypyridin-3-yl)(1-methoxy-5,6,7,8-tetrahydroisoquinolin-4-yl)amine | 286 (M + 1) |
| 22 | 6-(1-methoxy-5,6,7,8-tetrahydroisoquinolin-4-ylamino)-3H-isobenzofuran-1-one | 311 (M + 1) |
| 23 | (3-ethoxyphenyl)(1-methoxy-5,6,7,8-tetrahydroisoquinolin-4-yl)amine | 311 (M + 1) |
| 24 | (6-chloropyridin-3-yl)(1-methoxy-5,6,7,8-tetrahydroisoquinolin-4-yl)amine | 290 (M + 1) |
| 25 | 3-(1-methoxy-3-methyl-5,6,7,8-tetrahydroisoquinolin-4-ylamino)-N,N-dimethylbenzamide | 340 (M + 1) |
| 26 | (1-methoxy-3-methyl-5,6,7,8-tetrahydroisoquinolin-4-yl)(3-trifluoromethoxyphenyl)-amine | 353 (M + 1) |
| 27 | 1-[3-(1-methoxy-5,6,7,8-tetrahydroisoquinolin-4-ylamino)phenyl]ethanone | 297 (M + 1) |
| 28 | 1-[3-(1-methoxy-3-methyl-5,6,7,8-tetrahydroisoquinolin-4-ylamino)phenyl]ethanone | 311 (M + 1) |
| 29 | N-[3-(1-methoxy-3-methyl-5,6,7,8-tetrahydroisoquinolin-4-ylamino)phenyl]acetamide | 326 (M + 1) |

Synthesis of Compounds of the Formula X by Suzuki Coupling with Bromides of the Formula VI and Boronic Acids of the Formula $(OH)_2B—Ar—R''$ General Procedure 1 eq. of bromide (compound 8 or 9), 3.3 eq. of potassium iodide, 1.2 eq. of boronic acid are introduced under argon into absolute THF (3 ml/1 mmol). 0.05 eq. of Pd2dba3 and 0.1 eq. of tri-tert-butylphosphonium tetrafluoroborate are added, and the mixture is stirred at 60° C. for 15 h. After cooling, it is neutralized with saturated NaHCO3 solution and extracted twice with ethyl acetate, and the organic phase is concentrated. The residue is chromatographed on silica gel.

1-Methoxy-3-methyl-4-thiophen-2-yl-5,6,7,8-tetrahydroisoquinoline (Compound 30)

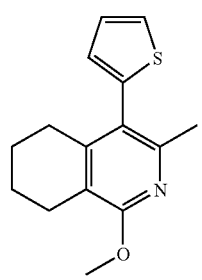

22 mg (31% yield) of compound 30 are obtained from 70 mg of bromide 8 in accordance with the general procedure
MS: m/z=260 (M+1)
1H-NMR (CDCl3): δ=7.37 (1H, dd, J=5.1, 1.1 Hz); 7.09 (1H, dd, J=5.1, 3.4 Hz); 6.79 (1H, dd, 3.4, 1.1 Hz); 3.96 (3H, s); 2.58 (2H, m); 2.40 (2H, m); 2.24 (3H, s); 1.70 (4H, m).

1-Methoxy-3-methyl-4-pyridin-3-yl-5,6,7,8-tetrahydroisoquinoline (Compound 31)

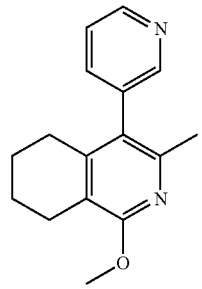

49 mg (49% yield) of compound 31 are obtained from 100 mg of bromide 8 in accordance with the general procedure.

MS: m/z=260 (M+1)

5-(1-Methoxy-5,6,7,8-tetrahydroisoquinolin-4-yl)furan-2-carbaldehyde (Compound 32)

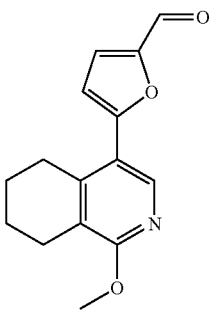

4.59 g (100% yield) of compound 32 are obtained from 4.32 g (17.9 mmol) of bromide 9 in accordance with the general procedure.

MS: m/z=258 (M+1)

5-(1-Methoxy-3-methyl-5,6,7,8-tetrahydroisoquinolin-4-yl)furan-2-carbaldehyde (Compound 33)

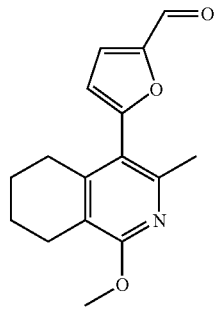

1.86 g (79% yield) of compound 33 are obtained from 2.0 g of bromide 8 in accordance with the general procedure.

MS: m/z=272 (M+1)

1H-NMR (CDCl3): δ=9.65 (1H, s); 7.34 (1H, d, J=3.4 Hz); 6.49 (1H, d, J=3.4 Hz); 3.96 (3H, s); 2.57 (2H, m); 2.46 (2H, m); 2.30 (3H, s); 1.71 (4H, m).

Synthesis of Compounds of the Formula X by Suzuki Coupling with Boronic Esters of the Formula VII and Bromides of the Formula Br—Ar—R3

The synthesis is shown for the following compound by way of example:

5-(1-Methoxy-5,6,7,8-tetrahydroisoquinolin-4-yl)nicotinic acid (Compound 34)

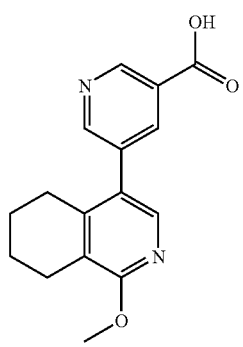

7.75 g (26.8 mmol) of boronic ester 11, 14.82 g (107.2 mmol) of potassium carbonate and 980 g (1.34 mmol) of PdCl2(dppf) are introduced into 60 ml of absolute DMF under argon, and 7 g (34.9 mmol) of 5-bromonicotinic acid are added. The mixture is stirred at 110° C. for 18 h, water is added, and the pH is adjusted to 4 with 2N HCL solution. Two extractions are carried out with DCM, and the organic phase is filtered and concentrated. The residue is taken up in 200 ml of DCM, mixed with activated carbon and filtered through Celite. The filtrate is concentrated and dried in a vacuum drying oven overnight. 7.4 g (97% yield) of dark crystals are obtained.

MS: m/z=285 (M+1)

Synthesis of Compounds 35-39 (Intermediates) by Deprotection of the Methoxy Group:

5-(1-Oxo-1,2,5,6,7,8-hexahydroisoquinolin-4-yl)furan-2-carbaldehyde (Compound 35)

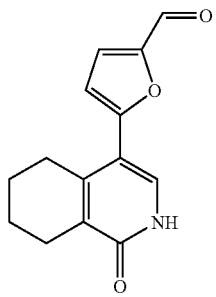

4.59 g (17.8 mmol) of compound 32 are suspended in 60 ml of acetonitrile. Addition of 3.26 g (19.6 mmol) of KI and 2.13 g (19.6 mmol) of trimethylchlorosilane is followed by treatment at 60° C. under argon for 6 h. The mixture is completely concentrated and the residue is treated with aqueous NaHCO3 solution. The remaining residue is then extracted 3× with DCM, and the organic phases are dried and concentrated. The residue is dissolved in 100 ml of EtOH, and Norit carbon is added. Filtration and concentration are carried out. About 1 g of the title compound is obtained. Further crude product is isolated from the carbon residue by extraction with DCM and is purified on silica gel. Overall yield: 2.38 g (55%) of white solid.

MS: m/z=244 (M+1)

1H-NMR (CDCl3): δ=12.6 (1H, s); 9.65 (1H, s); 7.75 (1H, s); 7.29 (1H, d, J=3.4 Hz); 6.56 (1H, d, J=3.4 Hz); 2.75 (2H, m); 2.62 (2H, m); 2.62 (2H, m); 1.70 (4H, m).

5-(3-Methyl-1-oxo-1,2,5,6,7,8-hexahydroisoquinolin-4-yl)furan-2-carbaldehyde (Compound 36)

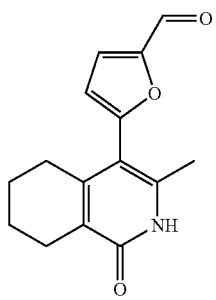

172 mg (27% yield) of the title compound are obtained in analogy to compound 35 from 660 mg (2.43 mmol) of compound 33 after purification by RP-HPLC.

MS: m/z=258 (M+1)

1H-NMR (CDCl3): δ=11.4 (1H, br s); 9.65 (1H, s); 7.35 (1H, d, J=3.4 Hz); 6.58 (1H, d, J=3.4 Hz); 2.61 (2H, m); 2.43 (2H, m); 2.35 (3H, s); 1.72 (4H, m).

5-(1-Oxo-1,2,5,6,7,8-hexahydroisoquinolin-4-yl)nicotinic acid (Compound 37)

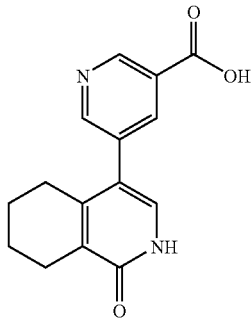

3.1 g (28.5 mmol) of compound 34 are suspended in 100 ml of acetonitrile. Addition of 4.73 g (28.5 mmol) of KI and 3.1 g (28.5 mmol) of trimethylchlorosilane is followed by heating at 80° C. under argon for 2 h. The mixture is cooled to RT, completely concentrated and taken up in 5:1 ethyl acetate/MeOH. The precipitate (4.78 g) is filtered off with suction and dried in a vacuum drying oven at 45° C. overnight. The mother liquor is concentrated and the residue is purified on silica gel. Overall yield: 5.64 g (81%) of beige solid.

MS: m/z=271 (M+1)

1H-NMR (D6-DMSO): δ=11.7 (1H, br s); 9.03 (1H, d, J=2.0 Hz); 8.74 (1H, d, J=2.2 Hz); 8.12 (1H, t, J=2.2 Hz); 2.41 (2H, m); 2.32 (2H, m); 1.63 (4H, m).

Ethyl 3-(1-oxo-1,2,5,6,7,8-hexahydroisoquinolin-4-ylamino)benzoate (Compound 38)

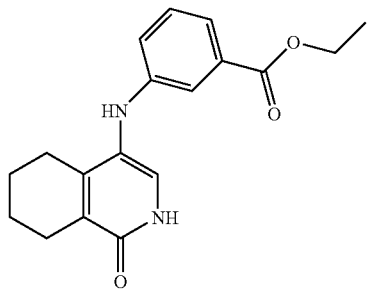

560 mg (1.7 mmol) of ethyl 3-(1-methoxy-5,6,7,8-tetrahydroisoquinolin-4-ylamino)benzoate (compound 12) are dissolved in 30 ml of chloroform and, at room temperature, 413 mg (2.1 mmol) of trimethylsilyl iodide are added. The mixture is then heated to reflux until complete conversion is reached by means of LCMS. Further trimethylsilyl iodide is added if necessary. For workup, the mixture is washed twice with $H_2O$, dried with $Na_2SO_4$ and concentrated. Chromatography on silica gel ($CH_2Cl_2$/MeOH 95:5) affords 216 mg of the title compound. Yield: 40%.

MS: m/z=313 (M+1)

3-(1-Oxo-1,2,5,6,7,8-hexahydroisoquinolin-4-ylamino)benzoic acid (Compound 39)

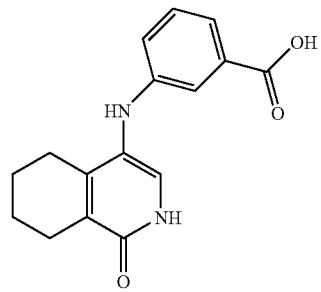

180 mg (0.58 mmol) of ethyl 3-(1-methoxy-5,6,7,8-tetrahydroisoquinolin-4-ylamino)benzoate (compound 38) are introduced into 3 ml of ethanol and, at room temperature, 3 ml of 2N KOH are added. After two hours, the solvent is removed in vacuo and the residue is taken up in 5 ml of $H_2O$ and acidified with 2N HCl. The resulting precipitate is filtered off with suction and dried. Yield: 123 mg (75%).

MS: m/z=285 (M+1)

Synthesis of tetrahydro-2H-isoquinolinones of the Formula I by Deprotection of the 1-methoxy-5,6,7,8-tetrahydroisoquinolines of the Formula VIII and X.

General Procedure 2 eq. of potassium iodide and 2 eq. of trimethylchlorosilane are added to a mixture of the 1-methoxy-5,6,7,8-tetrahydroisoquinolines of the formula VIII and IX in anhydrous acetonitrile (3-5 ml/mmol) under argon, and the turbid mixture is heated at 60-80° C. for 1-3 h. The mixture is then cooled to RT and concentrated. The crude product is purified by RP-HPLC, basic compounds being isolated as trifluoroacetates.

The following examples are synthesized in accordance with the general protocol:

| Example | Name | Mass(ES+) m/z = | NMR(D6-DMSO) δ = |
|---|---|---|---|
| 1 | 4-(3-hydroxyphenylamino)-5,6,7,8-tetrahydro-2H-isoquinolin-1-one | 257(M + 1) | |
| 2 | N-methyl-3-(1-oxo-1,2,5,6,7,8-hexahydroisoquinolin-4-ylamino)-benzamide | 298(M + 1) | |
| 3 | 4-(4-pyridin-4-ylthiazol-2-ylamino)-5,6,7,8-tetrahydro-2H-isoquinolin-1-one | 325(M + 1) | |

| Example | Name | Mass(ES+) m/z = | NMR(D6-DMSO) δ = |
|---|---|---|---|
| 4 | 4-(6-morpholin-4-ylpyridin-3-yl-amino)-5,6,7,8-tetrahydro-2H-isoquinolin-1-one | 325(M + 1) | |
| 5 | N-[3-(1-oxo-1,2,5,6,7,8-hexahydroisoquinolin-4-ylamino)-phenyl]acetamide | 298(M + 1) | |
| 6 | 4-(3-methanesulfonylphenyl-amino)-5,6,7,8-tetrahydro-2H-isoquinolin-1-one | 319(M + 1) | |
| 7 | 4-(3-methanesulfonylphenyl-amino)-3-methyl-5,6,7,8-tetrahydro-2H-isoquinolin-1-one | 333(M + 1) | 11.47(1H, br s), 7.48(1H, s), 7.32(1H, m); 7.09(1H, d, J=8.6 Hz), 6.95(1H, br s), 6.67(1H, br s), 3.13(3H, s), 2.33(4H, m), 2.01(3H, s), 1.58(4H, m) |
| 8 | 4-(3-hydroxymethylphenyl-amino)-5,6,7,8-tetrahydro-2H-isoquinolin-1-one | 271(M + 1) | |

4-(5-Hydroxymethylfuran-2-yl)-3-methyl-5,6,7,8-tetrahydro-2H-isoquinolin-1-one (Example 9)

The title compound is obtained as by-product in the reductive amination of 5-(3-methyl-1-oxo-1,2,5,6,7,8-hexahydroisoquinolin-4-yl)furan-2-carbaldehyde (compound 36) and is isolated by RP-HPLC.

MS: m/z=260 (M+1)

1H-NMR (D6-DMSO): δ=11.52 (1H, br s); 6.33 (1H, d, J=2.9 Hz); 6.27 (1H, d, J=2.9 Hz); 4.38 (2H, s); 2.33 (2H, m); 2.23 (2H, m); 2.03 (3H, s); 1.59 (4H, m).

Examples 10 to 19 which follow are prepared in accordance with Examples 1 to 8.

| Example | Name | Mass (ES+) m/z = | NMR(D6-DMSO) δ = |
|---|---|---|---|
| 10 | 4-(3-oxo-1,3-dihydrobenzofuran-5-ylamino)-5,6,7,8-tetrahydro-2H-isoquinolin-1-one | 297(M + 1) | |
| 11 | 4-(3-ethoxyphenylamino)-5,6,7,8-tetrahydro-2H-isoquinolin-1-one | 285(M + 1) | |
| 12 | 4-(6-chloropyridin-3-ylamino)-5,6,7,8-tetrahydro-2H-isoquinolin-1-one | 276(M + 1) | |
| 13 | N,N-dimethyl-3-(3-methyl-1-oxo-1,2,5,6,7,8-hexahydroisoquinolin-4-ylamino)benzamide | 326(M + 1) | |
| 14 | 3-methyl-4-(3-trifluoromethoxy-phenylamino)-5,6,7,8-tetrahydro-2H-isoquinolin-1-one | 339(M + 1) | |
| 15 | 4-(3-acetylphenylamino)-5,6,7,8-tetrahydro-2H-isoquinolin-1-one | 283(M + 1) | |
| 16 | 4-(3-acetylphenylamino)-3-methyl-5,6,7,8-tetrahydro-2H-isoquinolin-1-one | 297(M + 1) | 11.42(1H, br s), 7.21(2H, m), 7.18(1H, m), 6.98(1H, br s), 6.63(1H, br s), 2.48(3H, s), 2.32(4H, m), 2.00(3H, s), 1.57(4H, m) |
| 17 | N-[3-(3-methyl-1-oxo-1,2,5,6,7,8-hexahydroisoquinolin-4-ylamino)-phenyl]acetamide | 312(M + 1) | |
| 18 | 3-methyl-4-thiophen-2-yl-5,6,7,8-tetrahydro-2H-isoquinolin-1-one | 246(M + 1) | |
| 19 | 3-methyl-4-pyridin-3-yl-5,6,7,8-tetrahydro-2H-isoquinolin-1-one | 241(M + 1) | |

Synthesis of Examples 20-24 by Coupling Compound 39 with Amines

General Procedure 38 mg (0.13 mmol) of 3-(1-methoxy-5,6,7,8-tetrahydroisoquinolin-4-ylamino)benzoic acid are introduced into 2 ml of DMF and, at room temperature, 20 µl (0.15 mmol) of triethylamine are added. At 0° C., 52 mg (0.16 mmol) of TOTU are added, and the mixture is stirred at 0° C. for 15 min. After a further 30 minutes at room temperature, this solution is added to a second solution consisting of the respective amine (0.15 mmol), 20 µl (0.15 mmol) of triethylamine in 2 ml of DMF, and stirred at room temperature until complete conversion is found by LCMS. For workup, the solvent is removed and purification on silica gel is carried out.

The following compounds are prepared by the indicated general procedure:

N-Butyl-3-(1-oxo-1,2,5,6,7,8-hexahydroisoquinolin-4-ylamino)benzamide (Example 20)

Yield after silica gel chromatography ($CH_2Cl_2$/MeOH 95:5) 31%. $R_t$=1.166 min[1]); MS(M+H$^+$)=340.15; 500 MHz $^1$H-NMR (DMSO-$d_6$)[ppm]: 11.30, 1H, s, NH; 7.20-7.00, m, 5H, 4×aromat. H, NH; 6.62, dd, 1H, aromat. H, 3.20, m, 2H, $CH_2$; 2.33 m, 4H, 2×$CH_2$; 1.62, m, 2H, $CH_2$; 1.58, m, 2H, $CH_2$; 1.46, m, 2H, $CH_2$, 1.30, m, 2H, $CH_2$; 0.88, t, 3H, $CH_3$.

4-[3-(Pyrrolidin-1-carbonyl)phenylamino]-5,6,7,8-tetrahydro-2H-isoquinolin-1-one (Example 21)

Yield after silica gel chromatography ($CH_2Cl_2$/MeOH 95:5) 74% $R_t$=1.052 min[1]); MS(M+H$^+$)=338.15; 500 MHz $^1$H-NMR (DMSO-$d_6$)[ppm]: 11.30, 1H, s, NH; 7.22-7.05, m, 3H, 2×aromat. H, NH; 6.71, dd, 1H, aromat. H, 6.63-6.55, m, 2H, aromat. H, 3.08, m, 4H, 2×$CH_2$; 2.33, m, 4H, 2×$CH_2$; 1.90-1.73, m, 4H, 2×$CH_2$; 1.68-1.52, m, 4H, 2×$CH_2$.

4-[3-(4-Cyclopropylmethylpiperazine-1-carbonyl)phenylamino]-5,6,7,8-tetrahydro-2H-isoquinolin-1-one (Example 22)

Yield after silica gel chromatography ($CH_2Cl_2$/MeOH 95:5) 67%.
$R_t$=0.839 min[1]); MS(M+H$^+$)=407.25.

3-(1-Oxo-1,2,5,6,7,8-hexahydroisoquinolin-4-ylamino)-N-(2-pyridin-3-ylethyl)benzamide (Example 23)

Yield after silica gel chromatography (ethyl acetate/MeOH 10:1→4:1) 63%.
$R_t$=1.03 min[2]); MS(M+H$^+$)=389.11.

3-(1-Oxo-1,2,5,6,7,8-hexahydroisoquinolin-4-ylamino)-N-(2-pyrrolidin-1-ylethyl)benzamide (Example 24)

Yield after silica gel chromatography (ethyl acetate/MeOH 10:1→MeOH) 66%.
$R_t$=1.05 min[2]); MS(M+H$^+$)=381.15.

LCMS Method:
[1]) YMC J'sphere ODS H80 20×2, 4 µm;
   0 min 96% $H_2O$ (0.05% TFA) 2.0 min–95% ACN; 95% ACN to 2.4 min; 4% ACN 2.45 min;
   1 ml/min;
   30° C.
[2]) Col YMC J'sphere 33×2, 4 µm;
   Grad ACN+0.05% TFA: H2O+0.05% TFA 5.95 (0 min) to 95:5 (3.4 min) to 95:5 (4.4 min);
   1 ml/min;
   30° C.

Synthesis of Examples 25-49 by Coupling Compound 37 with Amines

General Procedure 54 mg (0.2 mmol) of 5-(1-oxo-1,2,5,6,7,8-hexahydroisoquinolin-4-yl)-nicotinic acid, 0.24 mmol of amine, 0.02 mmol of 4-DMAP, 0.8 mmol of N-methylmorpholine and 0.4 mmol of PPA (50% solution in DMF) are mixed in 3 ml of absolute DCM at RT and stirred for 18 h. The mixture is diluted with a little DCM and washed with saturated NaHCO3 solution, the organic phase is then concentrated and the residue is purified by RP-HPLC. Basic compounds are isolated as trifluoroacetates.

The following examples are prepared in accordance with the general protocol:

| Example | Name | Mass (ES+) m/z = | NMR(D6-DMSO) δ = |
|---|---|---|---|
| 25 | 4-[5-(pyrrolidine-1-carbonyl)-pyridin-3-yl]-5,6,7,8-tetrahydro-2H-isoquinolin-1-one | 324(M + 1) | |
| 26 | 5-(1-oxo-1,2,5,6,7,8-hexahydroisoquinolin-4-yl)-N-(2-oxo-2-phenylethyl)nicotinamide | 388(M + 1) | |
| 27 | 5-(1-oxo-1,2,5,6,7,8-hexahydroisoquinolin-4-yl)-N-phenethyl-nicotinamide | 374(M + 1) | |
| 28 | N-(4-nitrobenzyl)-5-(1-oxo-1,2,5,6,7,8-hexahydroisoquinolin-4-yl)nicotinamide | 405(M + 1) | |
| 29 | N-[2-(4-nitrophenyl)ethyl]-5-(1-oxo-1,2,5,6,7,8-hexahydroisoquinolin-4-yl)nicotinamide | 417(M + 1) | |
| 30 | N-[(4-nitrobenzoylamino)methyl]-5-(1-oxo-1,2,5,6,7,8-hexahydroisoquinolin-4-yl)nicotinamide | 433(M + 1) | |

-continued

| Example | Name | Mass (ES+) m/z = | NMR(D6-DMSO) δ = |
|---|---|---|---|
| 31 | N-[2-(4-pyridinecarbamoylaminoethyl)]-5-(1-oxo-1,2,5,6,7,8-hexahydroisoquinolin-4-yl)-nicotinamide | 418(M + 1) | |
| 32 | N-methyl-N-(3-nitrobenzyl)-5-(1-oxo-1,2,5,6,7,8-hexahydroisoquinolin-4-yl)nicotinamide | 419(M + 1) | |
| 33 | 5-(1-oxo-1,2,5,6,7,8-hexahydroisoquinolin-4-yl)-N-[2-(pyrimidin-2-ylamino)ethyl]nicotinamide | 391(M + 1) | |
| 34 | N-(5-methylisoxazol-3-ylmethyl)-5-(1-oxo-1,2,5,6,7,8-hexahydroisoquinolin-4-yl)nicotinamide | 365(M + 1) | |
| 35 | 5-(1-oxo-1,2,5,6,7,8-hexahydroisoquinolin-4-yl)-N-(1,3,5-trimethyl-1H-pyrazol-4-ylmethyl)-nicotinamide | 392(M + 1) | |
| 36 | 4-[5-(3-pyridin-4-ylpyrrolidine-1-carbonyl)pyridin-3-yl]-5,6,7,8-tetrahydro-2H-isoquinolin-1-one | 401(M + 1) | |
| 37 | N-(4-acetylaminobenzyl)-5-(1-oxo-1,2,5,6,7,8-hexahydroisoquinolin-4-yl)nicotinamide | 417(M + 1) | |
| 38 | N-methyl-5-(1-oxo-1,2,5,6,7,8-hexahydroisoquinolin-4-yl)-N-pyridin-4-ylmethylnicotinamide | 375(M + 1) | |
| 39 | N-(5-methylpyrazin-2-ylmethyl)-5-(1-oxo-1,2,5,6,7,8-hexahydroisoquinolin-4-yl)nicotinamide | 376(M + 1) | |
| 40 | 5-(1-oxo-1,2,5,6,7,8-hexahydroisoquinolin-4-yl)-N-(2-pyridin-3-ylethyl)nicotinamide | 375(M + 1) | |
| 41 | 5-(1-oxo-1,2,5,6,7,8-hexahydroisoquinolin-4-yl)-N-(3-phenyl-4,5-dihydroisoxazol-5-ylmethyl)-nicotinamide | 429(M + 1) | |
| 42 | N-(4-methanesulfonylbenzyl)-5-(1-oxo-1,2,5,6,7,8-hexahydroisoquinolin-4-yl)nicotinamide | 438(M + 1) | |
| 43 | 5-(1-oxo-1,2,5,6,7,8-hexahydroisoquinolin-4-yl)-N-(2-pyridin-4-ylethyl)nicotinamide | 375(M + 1) | 11.60(1H, br s), 8.88(1H, d, J=2.1 Hz), 8.78(1H, t, J=5.5 Hz), 8.74(2H, d, J=6.2 Hz), 8.65(1H, d, J=2.1 Hz), 8.03(1H, t, J=2.1 Hz), 7.80(2H, d, J=6.2 Hz), 7.18(1H, s); 3.65(2H, m), 3.10(2H, t, J=6.5 Hz); 2.41(2H, m), 2.31(2H, m), 1.69(2H, m), 1.59(2H, m). |
| 44 | 5-(1-oxo-1,2,5,6,7,8-hexahydroisoquinolin-4-yl)-N-[2-(4-sulfamoylphenyl)ethyl]nicotinamide | 453(M + 1) | |
| 45 | N-(3-methoxybenzyl)-5-(1-oxo-1,2,5,6,7,8-hexahydroisoquinolin-4-yl)nicotinamide | 390(M + 1) | 11.67(1H, br s), 9.23(1H, t, J=5.8Hz), 9.00(1H, d, J=1.9 Hz), 8.67(1H, d, J=2.1 Hz), 8.18(1H, t, J=2.0 Hz), 7.25(1H, t, J=8.0 Hz), 7.20(1H, s), 6.91(2H, m); 6.82(1H, m), 4.49(2H, d, J=5.8 Hz), 3.74(3H, s), 2.41(2H, m), 2.34(2H, m), 1.68(2H, m), 1.58(2H, m). |
| 46 | N-(2-methoxybenzyl)-5-(1-oxo-1,2,5,6,7,8-hexahydroisoquinolin-4-yl)nicotinamide | 390(M + 1) | |

-continued

| Example | Name | Mass (ES+) m/z = | NMR(D6-DMSO) δ = |
|---|---|---|---|
| 47 | N-(2,3-dimethoxybenzyl)-5-(1-oxo-1,2,5,6,7,8-hexahydroisoquinolin-4-yl)nicotinamide | 420(M + 1) | |
| 48 | 5-(1-oxo-1,2,5,6,7,8-hexahydroisoquinolin-4-yl)-N-pyridin-4-ylmethylnicotinamide | 361(M + 1) | |
| 49 | N-(1-ethylpyrrolidin-2-ylmethyl)-5-(1-oxo-1,2,5,6,7,8-hexahydroisoquinolin-4-yl)nicotinamide | 381(M + 1) | |

4-(5-Aminomethylfuran-2-yl)-5,6,7,8-tetrahydro-2H-isoquinolin-1-one (Example 50)

2.18 g (9.0 mmol) of compound 35 are dissolved with 844 mg (13.4 mmol) of NaCNBH4 and 55.3 g (717 mmol) of ammonium acetate in 160 ml of methanol/THF (5/1) and reacted at RT for 18 h. The yellow solution is completely concentrated and the residue is chromatographed on silica gel with ethyl acetate/methanol (1/1). The isolated compound, which still contains relatively large amounts of salt, is subsequently chromatographed by RP-HPLC. 400 mg of the title compound are isolated.

MS: m/z=245 (M+1)

Synthesis of Examples 51-79 by Reductive Amination of Compound 35 and 36 with Amines General Procedure 0.2 mmol of 5-(3-methyl-1-oxo-1,2,5,6,7,8-hexahydroisoquinolin-4-yl)furan-2-carbaldehyde or 5-(1-oxo-1,2,5,6,7,8-hexahydroisoquinolin-4-yl)furan-2-carbaldehyde and 0.24 mmol of amine are dissolved in 2 ml of THF and, after addition of about 0.5 mmol of MP triacetoxyborohydrides, shaken at RT for 18 h. The solution is filtered off, the resin is washed twice with 4 ml of THF each time, and the complete organic phase is concentrated and purified by RP-HPLC. The compounds are isolated as trifluoroacetates after freeze drying.

| Example | Name | Mass (Es+) m/z = | NMR(D6-DMSO) δ = |
|---|---|---|---|
| 51 | 4-[5-(benzylaminomethyl)furan-2-yl]-3-methyl-5,6,7,8-tetrahydro-2H-isoquinolin-1-one | 349(M + 1) | |
| 52 | 3-methyl-4-(5-{[(1-methyl-1H-pyrazol-4-ylmethyl)amino]methyl}-furan-2-yl)-5,6,7,8-tetrahydro-2H-isoquinolin-1-one | 353(M + 1) | |
| 53 | 4-(5-butylaminomethylfuran-2-yl)-3-methyl-5,6,7,8-tetrahydro-2H-isoquinolin-1-one | 315(M + 1) | |
| 54 | 3-methyl-4-(5-pyrrolidin-1-ylmethylfuran-2-yl)-5,6,7,8-tetrahydro-2H-isoquinolin-1-one | 313(M + 1) | 11.62(1H, br s), 10.03(1H, br s), 6.74(1H, d, J=3.4 Hz), 6.47(1H, d, J=3.4 Hz), 4.46(2H, d, J=5.2 Hz), 3.40(2H, m), 3.11(2H, m), 2.34(2H, m), 2.23(2H, m), 2.04(3H, s), 1.86(2H, m), 1.62(4H, m). |
| 55 | 4-(5-{[(1-methyl-1H-benzoimidazol-2-ylmethyl)amino]methyl}furan-2-yl)-5,6,7,8-tetrahydro-2H-isoquinolin-1-one | 389(M + 1) | |
| 56 | 4-[5-(4-pyrimidin-2-ylpiperazin-1-ylmethyl)furan-2-yl]-5,6,7,8-tetrahydro-2H-isoquinolin-1-one | 392(M + 1) | |
| 57 | 4-{5-[(2-pyrrolidin-1-ylethylamino)-methyl]furan-2-yl}-5,6,7,8-tetrahydro-2H-isoquinolin-1-one | 342(M + 1) | |
| 58 | 4-(5-{[(pyridin-4-ylmethyl)amino]-methyl}furan-2-yl)-5,6,7,8-tetrahydro-2H-isoquinolin-1-one | 336(M + 1) | |

-continued

| Example | Name | Mass (Es+) m/z = | NMR(D6-DMSO) δ = |
|---|---|---|---|
| 59 | 4-(5-{[(pyridin-3-ylmethyl)amino]-methyl}furan-2-yl)-5,6,7,8-tetrahydro-2H-isoquinolin-1-one | 336(M + 1) | |
| 60 | 4-(5-{[2-(1-methylpyrrolidin-2-yl)-ethylamino]methyl}furan-2-yl)-5,6,7,8-tetrahydro-2H-isoquinolin-1-one | 356(M + 1) | |
| 61 | 4-(5-pyrrolidin-1-ylmethylfuran-2-yl)-5,6,7,8-tetrahydro-2H-isoquinolin-1-one | 299(M + 1) | |
| 62 | 4-(5-{[(pyridin-2-ylmethyl)amino]-methyl}furan-2-yl)-5,6,7,8-tetrahydro-2H-isoquinolin-1-one | 336(M + 1) | |
| 63 | 4-[5-(3-hydroxypyrrolidin-1-ylmethyl)furan-2-yl]-5,6,7,8-tetrahydro-2H-isoquinolin-1-one | 315(M + 1) | |
| 64 | 4-(5-{[(4-pyrrolidin-1-ylpiperidin-1-ylmethyl)amino]methyl}furan-2-yl)-5,6,7,8-tetrahydro-2H-isoquinolin-1-one | 411(M + 1) | |
| 65 | 4-{5-[(2-dimethylaminoethyl-amino)methyl]furan-2-yl}-5,6,7,8-tetrahydro-2H-isoquinolin-1-one | 316(M + 1) | |
| 66 | 4-(5-{[methyl-(4,5,6,7-tetrahydro-benzothiazol-2-ylmethyl)amino]-methyl}furan-2-yl)-5,6,7,8-tetrahydro-2H-isoquinolin-1-one | 410(M + 1) | |
| 67 | 4-[5-(2-pyridin-2-ylpyrrolidin-1-ylmethyl)furan-2-yl]-5,6,7,8-tetrahydro-2H-isoquinolin-1-one | 376(M + 1) | |
| 68 | 4-(5-{[(1H-benzimidazol-2-ylmethyl)amino]methyl}furan-2-yl)-5,6,7,8-tetrahydro-2H-isoquinolin-1-one | 375(M + 1) | |
| 69 | 4-(5-{[benzyl(1-methyl-1H-imidazol-2-ylmethyl)amino]-methyl}furan-2-yl)-5,6,7,8-tetrahydro-2H-isoquinolin-1-one | 429(M + 1) | |
| 70 | 4-[5-(indan-2-ylaminomethyl)-furan-2-yl]-5,6,7,8-tetrahydro-2H-isoquinolin-1-one | 361(M + 1) | |
| 71 | 4-[5-({4-(4-fluorophenyl)-piperazin-1-yl]-5,6,7,8-tetrahydro-2H-isoquinolin-1-one | 437M + 1) | |
| 72 | 4-{5-[(2-hydroxy-2-phenyl-ethylamino)methyl]furan-2-yl}-5,6,7,8-tetrahydro-2H-isoquinolin-1-one | 365(M + 1) | 11.75(1H, br s), 9.14(2H, br s), 7.46(1H, s), 7.41-7.31(5H, m), 6.67(1H, d, J=3.1 Hz), 6.52(1H, d, J=3.1 Hz), 6.21(1H, d, J=3.4 Hz); 4.90(1H, m), 4.30(2H, br s), 3.11(1H, m), 2.99(1H, m), 2.56(2H, m), 2.38 2H, m), 1.65 4H, m) |
| 73 | 4-(5-{[(4-methylpiperazin-1-ylmethyl)amino]methyl}furan-2-yl)-5,6,7,8-tetrahydro-2H-isoquinolin-1-one | 357(M + 1) | |
| 74 | 4-(5-{[(morpholin-4-ylmethyl)-amino]methyl}furan-2-yl)-5,6,7,8-tetrahydro-2H-isoquinolin-1-one | 344(M + 1) | |
| 75 | N-[4-({[5-(1-oxo-1,2,5,6,7,8-hexahydroisoquinolin-4-yl)furan-2-ylmethyl]amino}methyl)phenyl]-acetamide | 392(M + 1) | |
| 76 | 4-(5-thiazolidin-3-ylmethylfuran-2-yl)-5,6,7,8-tetrahydro-2H-isoquinolin-1-one | 317(M + 1) | |
| 77 | 4-(5-{[(1-methyl-1H-pyrazol-4- | 339(M + 1) | (CDCl3) 7.68(1H, |

| Example | Name | Mass (Es+) m/z = | NMR(D6-DMSO) δ = |
|---|---|---|---|
| | ylmethyl)amino]methyl}furan-2-yl)-5,6,7,8-tetrahydro-2H-isoquinolin-1-one | | s), 7.62(1H, s), 7.16(1H, s), 6.42(1H, d, J=3.4 Hz), 6.27(1H, d, J=3.4 Hz), 4.18(2H, s), 4.09(2H, s), 3.90(3H, s), 2.55(2H, m), 2.39(2H, m), 1.68(4H, m) |
| 78 | 4-(5-butylaminomethylfuran-2-yl)-5,6,7,8-tetrahydro-2H-isoquinolin-1-one | 301(M + 1) | |
| 79 | 4-[5-(benzylaminomethyl)furan-2-yl]-5,6,7,8-tetrahydro-2H-isoquinolin-1-one | 335(M + 1) | |

Synthesis of Examples 80-84 by Acylation of Example 50 with Carboxylic Acids

General Procedure 0.15 mmol of 4-(5-aminomethylfuran-2-yl)-5,6,7,8-tetrahydro-2H-isoquinolin-1-one are dissolved together with 0.15 mmol of acid chloride or acid anhydride and 0.375 mmol of triethylamine in 5 ml of DCM and stirred at 0° C. for 2 h. The reaction mixture is mixed with water and extracted with DCM, and the organic phase is concentrated and purified by RP-HPLC. Example 84 is isolated as trifluoroacetate.

The following compounds are prepared in accordance with the general protocol:

| Example | Name | Mass (ES+) m/z = | NMR(D6-DMSO) δ = |
|---|---|---|---|
| 80 | 2,2,2-trifluoro-N-[5-(1-oxo-1,2,5,6,7,8-hexahydroisoquinolin-4-yl)furan-2-ylmethyl]acetamide | 341 | 11.62(1H, br s), 9.99(1H, s), 7.34(1H, s), 6.42(1H, d, J=3.4 Hz), 6.37(1H, d, J=3.4 Hz), 4.42(2H, d, J=5.8 Hz), 2.55(2H, m), 2.37(2H, m), 1.65(4H, m). |
| 81 | 3-methyl-N-[5-(1-oxo-1,2,5,6,7,8-hexahydroisoquinolin-4-yl)furan-2-ylmethyl]butyramide | 329 | |
| 82 | N-[5-(1-oxo-1,2,5,6,7,8-hexahydroisoquinolin-4-yl)furan-2-ylmethyl]furan-2-carboxamide | 339 | |
| 83 | 4-methoxy-N-[5-(1-oxo-1,2,5,6,7,8-hexahydroisoquinolin-4-yl)furan-2-ylmethyl]benzamide | 379 | 11.6(1H, br s); 8.83(1H, t, J=5.5Hz); 7.86(2H, d, J=8.9 Hz); 7.33(1H, s); 7.00(2H, d, J=8.9 Hz); 6.39(1H, d, J=3.1 Hz); 6.30(1H, d, J=3.1 Hz); 4.46(2H, d, J=5.5 Hz); 3.80(3H, s); 2.55(2H, m); 2.37(2H, m); 1.64(4H, m). |
| 84 | N-[5-(1-oxo-1,2,5,6,7,8-hexahydroisoquinolin-4-yl)furan-2-ylmethyl]nicotinamide | 350 | |

Synthesis of Examples 85-87 by Reacting Example 50 with Sulfonyl Chlorides

General Procedure 0.15 mmol of 4-(5-aminomethylfuran-2-yl)-5,6,7,8-tetrahydro-2H-isoquinolin-1-one are dissolved together with 0.18 mmol of sulfonyl chloride and 0.375 mmol of potassium carbonate in 5 ml of DCM and stirred at RT for 18 h. The reaction mixture is mixed with water and extracted with DCM, and the organic phase is concentrated and purified by RP-HPLC. Example 85 is isolated as trifluoroacetate.

| Example | Name | Mass (ES+) m/z = | NMR(D6-DMSO) δ = |
|---|---|---|---|
| 85 | N-[5-(1-oxo-1,2,5,6,7,8-hexahydroisoquinolin-4-yl)furan-2-ylmethyl]-4-(pyridin-2-yloxy)benzenesulfonamide | 592 | |
| 86 | 3-methoxy-N-[5-(1-oxo-1,2,5,6,7,8-hexahydroisoquinolin-4-yl)furan-2-ylmethyl]benzenesulfonamide | 415 | |
| 87 | N-(4-{[5-(1-oxo-1,2,5,6,7,8-hexahydroisoquinolin-4-yl)furan-2-ylmethyl]sulfamoyl}phenyl)acetamide | 442 | 11.6(1H, br s); 10.22(1H, s); 8.06(1H, t, J=5.8 Hz); 7.65(4H, m); 7.24(1H, s); 6.26(1H, d, J=3.1 Hz); 6.29(1H, d, J=3.1 Hz); 4.02(2H, d, J=5.8 Hz); 2.45(2H, m); 2.36(2H, m); 2.06(3H, s); 1.63(4H, m). |

Pharmacological Investigations

PARP Enzyme Assay

The half-maximum inhibitor concentration is determined by incubating the substances to be tested with the DNA-activated, recombinantly expressed and purified PARP-1 enzyme. Specifically, various concentrations of the test substance are incubated in 50 µl of reaction solution, which contains 50 mM Tris, 5 mM $MgCl_2$, 1 mM DTT, 200 µM NAD, 0.1 mCi/ml tritium-labeled NAD, 0.1 mg/ml DNA, 0.1 mg/ml histones, 2 µg/ml recombinantly expressed human PARP-1 enzyme, pH=8.0, at room temperature for 1 hour. The reaction is stopped by adding 150 µl of 20% trichloroacetic acid, and the radiolabeled protein constituents are precipitated. After incubation on ice for 10 minutes, the labeled, insoluble constituents are separated off through a glass fiber filter and, after washing with 20% trichloroacetic acid three times, the radioactivity incorporated by the PARP-1 enzyme is measured by radioluminescence. Consideration of the incorporation rates determined in this way as a function of the concentration of the test substance results in the half-maximum inhibitor concentration ($IC_{50}$) as the concentration of the test substance which reduces the incorporation rate to half the maximum value attainable (incubation without inhibitor).

IC-50 values were determined in this way for the following compounds:

| Ex. | IC-50 [µM] | Ex. | IC-50 [µM] | Ex. | IC-50 [µM] |
|---|---|---|---|---|---|
| 1 | 1.31 | 2 | 0.27 | 3 | 9.83 |
| 4 | 6.35 | 5 | 0.39 | 6 | 0.80 |
| 7 | 0.30 | 8 | 0.61 | 9 | 0.28 |
| 10 | 1.43 | 11 | 0.39 | 12 | 0.67 |
| 13 | 0.08 | 14 | 1.21 | 15 | 0.69 |
| 16 | 0.09 | 17 | 0.14 | 18 | 0.38 |
| 19 | 0.74 | 20 | 1.28 | 21 | 10.58 |
| 22 | 0.33 | 23 | 2.01 | 24 | 0.22 |
| 25 | 7.70 | 26 | 1.47 | 27 | 2.54 |
| 28 | 0.40 | 29 | 0.56 | 30 | 3.35 |
| 31 | 4.80 | 32 | 0.77 | 33 | 3.69 |
| 34 | 3.48 | 35 | 6.88 | 36 | 0.42 |
| 37 | 4.07 | 38 | 3.19 | 39 | 5.89 |
| 40 | 4.69 | 41 | 3.85 | 42 | 1.03 |
| 43 | 0.82 | 44 | 8.27 | 45 | 1.70 |
| 46 | 3.13 | 47 | 3.29 | 48 | 3.07 |
| 49 | 5.11 | 51 | 0.59 | 52 | 0.33 |
| 53 | 0.24 | 54 | 0.30 | 55 | 4.54 |
| 56 | 1.45 | 57 | 0.42 | 58 | 1.27 |
| 59 | 0.99 | 60 | 0.56 | 61 | 0.11 |
| 62 | 1.53 | 63 | 0.24 | 64 | 0.34 |
| 65 | 0.46 | 66 | 1.18 | 67 | 0.72 |
| 68 | 0.34 | 69 | 2.76 | 70 | 0.31 |
| 71 | 1.24 | 72 | 0.11 | 73 | 0.66 |
| 74 | 0.74 | 75 | 0.51 | 76 | 0.44 |
| 77 | 0.18 | 78 | 0.25 | 79 | 0.15 |
| 80 | 0.54 | 81 | 1.07 | 82 | 0.46 |
| 83 | 1.25 | 84 | 0.79 | 85 | 1.63 |
| 86 | 2.48 | 87 | 3.77 | | |

ATP Consumption Assay in Cardiomyoblasts

The activity of the test substances in cells is ascertained by means of an ATP consumption assay. For this purpose, rat cardiomyocytes (H9c2 cell line) are seeded in a 96-well plate (40 000 cells per well, RPMI1640; 10% FCS) and kept at 37° C. and 5% $CO_2$ for 16 hours. The cells are washed with PBS and incubated under identical conditions with various concentrations of the test substance in medium for 15 min. After addition of 300 µM $H_2O_2$, the cells are kept at 37° C., 5% $CO_2$ for a further hour and lysed, and the cellular content of ATP is determined by means of luciferase reaction. The half-maximum effective concentration of the substances (EC50) is determined as the concentration at which the ATP content of the cells has reached half the value which can be measured with a maximally effective concentration of the same substance.

Enzyme Inhibition Assay with Various Substrate Concentrations

Apparent $K_i$ values of the test substances are determined in an enzymatic assay using the purified human PARP-1 enzyme. Specifically, various concentrations of the tritium-labeled substrate NAD are incubated with an identical concentration of the test substance in 50 µl of reaction solution, which contains 50 mM tris, 5 mM MgCl2, 1 mM DTT, 0.1 mg/ml DNA, 0.1 mg/ml histones, 2 µg/ml recombinantly expressed human PARP-1 enzyme, pH=8.0, at room temperature for 10 min. The reaction is stopped by adding 150 µl of 20% trichloroacetic acid, and the radiolabeled protein constituents are precipitated. After incubation on ice for 10 minutes, the labeled, insoluble constituents are separated off through a glass fiber filter and, after washing with 20% trichloroacetic acid three times, the radioactivity incorporated by the PARP-1 enzyme is measured by radioluminescence. Evaluation of the incorporation rates determined in this way as a function of the concentration of the substrate NAD affords the apparent $K_i$ values according to Michaelis-Menten kinetics, assuming that the mechanism of inhibition is purely competitive.

EC-50 values and apparent $K_i$ values are determined in this way for all the following selected compounds:

| Ex. | EC-50 [µM] | app. $K_i$ [nM] | Ex. | EC-50 [µM] | app. $K_i$ [nM] |
|---|---|---|---|---|---|
| 9 | 1.57 | 16 | 54 | 0.33 | 15 |
| 16 | 0.2 | 54 | 72 | 0.38 | 24 |
| 24 | — | 31 | 78 | 0.52 | 40 |

What is claimed is:

1. A compound of the formula (I)

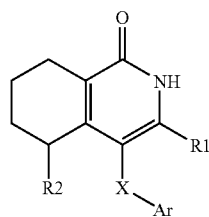

(I)

in which the meanings are:
X is a single bond, O, S, NH or N($C_1$-$C_3$-alkyl);
R1 is hydrogen, fluorine, chlorine, —CN, methoxy, —OCF$_3$ or $C_1$-$C_3$-alkyl which is optionally substituted by hydroxy, chlorine, methoxy or one, two or three fluorine atoms;
R2 is hydrogen, fluorine, —CN, hydroxy, methoxy, —OCF$_3$, —NH$_2$, —NH($C_1$-$C_3$-alkyl), —N($C_1$-$C_3$-alkyl)$_2$ or $C_1$-$C_3$-alkyl which is optionally substituted by hydroxy, chlorine, methoxy or one, two or three fluorine atoms;
R3 is —($C_1$-$C_3$-alkyl)—NR4R5, —SO$_2$NR4R5, —C(O)NR4R5, —C(H)=N—OR9, —C(O)R6, —NHC(O)R6, —($C_1$-$C_3$-alkyl)—NHC(O)R6, —NHSO$_2$R6, —($C_1$-$C_3$-alkyl)—NHSO$_2$R6 or —CH(OH)R7;

R4 and R5 are independently of one another selected from the group consisting of:
hydrogen; unsubstituted or at least monosubstituted $C_1$-$C_{10}$-alkyl, $C_2$-$C_6$-alkenyl, $C_2$-$C_6$-alkynyl, aryl, heteroaryl and heterocyclyl,
where the substituents are selected from the group consisting of: aryl, heteroaryl, heterocyclyl, —O-aryl, fluorine, chlorine, bromine, —CF$_3$, —OCF$_3$, —NO$_2$, —CN, —C(O)R8, —NHC(O)($C_1$-$C_3$-alkyl), —NH$_2$, hydroxy, $C_1$-$C_6$-alkyl, $C_1$-$C_3$-alkoxy, —NH($C_1$-$C_3$-alkyl), —N($C_1$-$C_3$-alkyl)$_2$, —NH-aryl, —NH-heteroaryl, —NH—C(O)-heteroaryl, —SO$_2$NH$_2$, —SO$_2$($C_1$-$C_3$-alkyl) and —NH—SO$_2$($C_1$-$C_3$-alkyl),
and the aryl, heteroaryl and heterocyclyl fragments of these substituents may in turn be at least monosubstituted by fluorine, chlorine, bromine, oxo, —CF$_3$, —OCF$_3$, —NO$_2$, —CN, aryl, heteroaryl, —NHC(O)($C_1$-$C_3$-alkyl), —COOH, hydroxy, $C_1$-$C_3$-alkyl, $C_1$-$C_3$-alkoxy, —SO$_2$NH$_2$, —SO$_2$NH($C_1$-$C_3$-alkyl), —SO$_2$N($C_1$-$C_3$-alkyl)$_2$, —C(O)NH$_2$, —C(O)NH($C_1$-$C_3$-alkyl), —C(O)N($C_1$-$C_3$-alkyl)$_2$, —SO$_2$($C_1$-$C_3$-alkyl), —NH$_2$, —NH($C_1$-$C_3$-alkyl) or —N($C_1$-$C_3$-alkyl)$_2$; or
R4 and R5 form together with the nitrogen atom to which they are bonded unsubstituted or at least monosubstituted heterocyclyl,
where the substituents are selected from the group consisting of: aryl, heteroaryl, heterocyclyl, oxo, fluorine, chlorine, bromine, —CF$_3$, —OCF$_3$, —NO$_2$, —CN, —C(O)R8, —NHC(O)($C_1$-$C_3$-alkyl), —NH$_2$, hydroxy, $C_1$-$C_3$-alkyl, $C_1$-$C_3$-alkoxy, —NH($C_1$-$C_3$-alkyl), —N($C_1$-$C_3$-alkyl)$_2$, —SO$_2$NH$_2$, —SO$_2$($C_1$-$C_3$-alkyl) and —NH—SO$_2$($C_1$-$C_3$-alkyl),
and, of these substituents, aryl, heterocyclyl and heteroaryl in turn may be at least monosubstituted by fluorine, chlorine, bromine, hydroxy, $C_1$-$C_3$-alkyl or $C_1$-$C_3$-alkoxy;
R6 is unsubstituted or at least monosubstituted $C_1$-$C_6$-alkyl, phenyl, heteroaryl or heterocyclyl,
where the substituents are selected from the group consisting of: fluorine, chlorine bromine, aryl, heterocyclyl, heteroaryl, —CF$_3$, —OCF$_3$, —NO$_2$, —CN, —C(O)R8, —NHC(O)($C_1$-$C_3$-alkyl), —NH$_2$, hydroxy, $C_1$-$C_3$-alkyl, $C_1$-$C_3$-alkoxy, —O-heteroaryl, —O-aryl, —NH($C_1$-$C_3$-alkyl), —N($C_1$-$C_3$-alkyl)$_2$, —SO$_2$NH$_2$, —SO$_2$($C_1$-$C_3$-alkyl) and —NH—SO$_2$($C_1$-$C_3$-alkyl),
and the aryl, heterocyclyl and heteroaryl fragments of these substituents may in turn be at least monosubstituted by fluorine, chlorine, bromine, hydroxy, $C_1$-$C_3$-alkyl or $C_1$-$C_3$-alkoxy;
R7 is selected from the group consisting of:
hydrogen; unsubstituted or at least monosubstituted $C_1$-$C_6$-alkyl, phenyl and heteroaryl,
where the substituents are selected from the group consisting of:
fluorine, chlorine, bromine, —CF$_3$, —OCF$_3$, —NO$_2$, —CN, —C(O)R8, —NHC(O)($C_1$-$C_3$-alkyl), —NH$_2$, hydroxy, $C_1$-$C_3$-alkyl, $C_1$-$C_3$-alkoxy, —NH($C_1$-$C_3$-alkyl), —N($C_1$-$C_3$-alkyl)$_2$, —SO$_2$NH$_2$, —SO$_2$($C_1$-$C_3$-alkyl) and —NH—SO$_2$($C_1$-$C_3$-alkyl);
R8 is $C_1$-$C_3$-alkoxy, —O-phenyl, $C_1$-$C_3$-alkyl, —NH$_2$, —NH($C_1$-$C_3$-alkyl), —N($C_1$-$C_3$-alkyl)$_2$ or phenyl,
and the above phenyl fragments may in turn be at least monosubstituted by fluorine, chlorine, bromine, oxo, —CF$_3$, —OCF$_3$, —NO$_2$, —CN, aryl, heteroaryl, —NHC(O)($C_1$-$C_3$-alkyl), —COOH, hydroxy, $C_1$-$C_3$- alkyl, $C_1$-$C_3$-alkoxy, —$SO_2NH_2$, —$SO_2NH(C_1$-$C_3$-alkyl), —$SO_2N(C_1$-$C_3$-alkyl)$_2$, —C(O)$NH_2$, —C(O)NH($C_1$-$C_3$-alkyl), —C(O)N($C_1$-$C_3$-alkyl)$_2$, —$SO_2$($C_1$-$C_3$-alkyl), —$NH_2$, —NH($C_1$-$C_3$-alkyl) or —N($C_1$-$C_3$-alkyl)$_2$ R9 is selected from the group consisting of:
  hydrogen; unsubstituted or at least monosubstituted $C_1$-$C_6$-alkyl and phenyl,
    where the substituents are selected from the group consisting of:
  fluorine, chlorine, bromine, aryl, heterocyclyl, heteroaryl, —$CF_3$, —$OCF_3$, —$NO_2$, —CN, —C(O)R8, —NHC(O)($C_1$-$C_3$-alkyl), $C_1$-$C_3$-alkyl, $C_1$-$C_3$-alkoxy, —NH($C_1$-$C_3$-alkyl), —N($C_1$-$C_3$-alkyl)$_2$, —$SO_2NH_2$, —$SO_2$($C_1$-$C_3$-alkyl) and —NH—$SO_2$($C_1$-$C_3$-alkyl),
    and, of these substituents, aryl, heterocyclyl and heteroaryl may in turn be at least monosubstituted by fluorine, chlorine, bromine, $C_1$-$C_3$-alkyl or $C_1$-$C_3$-alkoxy;

Ar is unsubstituted or at least monosubstituted aryl or heteroaryl, where the substituents are selected from the group consisting of: fluorine, chlorine, bromine, —$CF_3$, —$OCF_3$, —$NO_2$, —CN, —C(O)R8, —$NH_2$, —NHC(O)($C_1$-$C_6$-alkyl), hydroxy, $C_1$-$C_6$-alkyl, $C_1$-$C_6$-alkoxy, —$CH_2$—$CH_2$—$CH_2$—, —$CH_2$—O—C(O)—, —$CH_2$—C(O)—O—, —$CH_2$—NH—C(O)—, —$CH_2$—N($CH_3$)—C(O)—, —$CH_2$—C(O)—NH—, —NH($C_1$-$C_6$-alkyl), —N($C_1$-$C_6$-alkyl)$_2$, —$SO_2$($C_1$-$C_6$-alkyl), heterocyclyl, heteroaryl, aryl and R3,
    and, of these substituents, heterocyclyl, aryl and heteroaryl may in turn be at least monosubstituted by $C_1$-$C_6$-alkyl, $C_1$-$C_6$-alkoxy, fluorine, chlorine, bromine, trifluoromethyl, trifluoromethoxy or OH;

heteroaryl is a 5 to 10-membered, aromatic, mono- or bicyclic heterocycle which comprises one or more heteroatoms selected from N, O and S;
aryl is a 5 to 10-membered, aromatic, mono- or bicycle; and
heterocyclyl is a 5 to 10-membered, non-aromatic, mono- or bicyclic heterocycle which comprises one or more heteroatoms selected from N, O and S;
or a physiologically tolerated salt thereof.
provided that Ar is not unsubstituted phenyl when X is a single bond.

2. A compound as claimed in claim 1, in which the meanings in the formula (I) are:
X is a single bond, NH or N($C_1$-$C_3$-alkyl);
R1 is hydrogen or $C_1$-$C_3$-alkyl which is optionally substituted by hydroxy, chlorine, methoxy or one, two or three fluorine atoms;
R2 is hydrogen, fluorine, —$OCF_3$, hydroxy, methoxy, —$NH_2$ or $C_1$-$C_3$-alkyl;
R3 is —$CH_2$—NR4R5, —$SO_2$NR4R5, —C(O)NR4R5, —$CH_2$—NHC(O)R6, —$CH_2$—NHSO$_2$R6 or —CH(OH)R7;
R4 and R5 are independently of one another selected from the group consisting of:
  hydrogen; unsubstituted or at least monosubstituted $C_1$-$C_{10}$-alkyl, $C_2$-$C_6$-alkenyl, phenyl, indanyl, heterocyclyl and heteroaryl,
    where the substituents are selected from the group consisting of: phenyl, heteroaryl, heterocyclyl, —O-phenyl, fluorine, —CN, —C(O)$NH_2$, —C(O)($C_1$-$C_3$-alkyl), —C(O)-phenyl, —N($C_1$-$C_3$-alkyl)$_2$, —NH($C_1$-$C_3$-alkyl), —$NH_2$, —NH-heteroaryl, —NH—C(O)-heteroaryl, $C_1$-$C_6$-alkyl, $C_1$-$C_3$-alkoxy and hydroxy,
    and the phenyl, heterocyclyl and heteroaryl fragments of these substituents may in turn be at least monosubstituted by fluorine, chlorine, bromine, oxo, —$CF_3$, —$OCF_3$, —$NO_2$, —CN, phenyl, pyrimidinyl, —NHC(O)($C_1$-$C_3$-alkyl), —COOH, hydroxy, $C_1$-$C_3$-alkyl, $C_1$-$C_3$-alkoxy, —$SO_2NH_2$, —$SO_2$NH($C_1$-$C_3$-alkyl), —$SO_2$N($C_1$-$C_3$-alkyl)$_2$, —C(O)$NH_2$, —C(O)NH($C_1$-$C_3$-alkyl), —C(O)N($C_1$-$C_3$-alkyl)$_2$, —$SO_2$($C_1$-$C_3$-alkyl), —$NH_2$, —NH($C_1$-$C_3$-alkyl) or —N($C_1$-$C_3$-alkyl)$_2$; or R4 and R5 form together with the nitrogen atom to which they are bonded unsubstituted or at least monosubstituted heterocyclyl,
  where the substituents are selected from the group consisting of: phenyl, heteroaryl, heterocyclyl, oxo, fluorine, chlorine, —C(O)($C_1$-$C_3$-alkyl), —C(O)-phenyl and hydroxy,
  and the phenyl, heterocyclyl and heteroaryl fragments of these substituents may in turn be at least monosubstituted by fluorine or $C_1$-$C_3$-alkyl;

R6 is unsubstituted or at least monosubstituted $C_1$-$C_6$-alkyl, phenyl or heteroaryl,
  where the substituents are selected from the group consisting of: fluorine, chlorine, bromine, —$CF_3$, —$OCF_3$, —NHC(O)($C_1$-$C_3$-alkyl), hydroxy, $C_1$-$C_3$-alkyl, $C_1$-$C_3$-alkoxy, —O-heteroaryl, phenyl, —$NH_2$, —NH($C_1$-$C_3$-alkyl), —N($C_1$-$C_3$-alkyl)$_2$ and heterocyclyl,
  and the phenyl, heteroaryl and heterocyclyl fragments of these substituents may in turn be at least monosubstituted by fluorine, chlorine, bromine, hydroxy, $C_1$-$C_3$-alkyl or $C_1$-$C_3$-alkoxy;

R7 is selected from the group consisting of:
  hydrogen; unsubstituted or at least monosubstituted $C_1$-$C_6$-alkyl, phenyl and pyridinyl,
    where the substituents are selected from the group consisting of: fluorine, chlorine, bromine, hydroxy, $C_1$-$C_3$-alkyl and $C_1$-$C_3$-alkoxy;

Ar is unsubstituted or at least monosubstituted phenyl or heteroaryl,
  where the substituents are selected from the group consisting of: fluorine, chlorine, —$CF_3$, —$OCF_3$, C(O)($C_1$-$C_3$-alkyl), —$NH_2$, —NHC(O)($C_1$-$C_3$-alkyl), hydroxy, $C_1$-$C_3$-alkyl, $C_1$-$C_3$-alkoxy, —$CH_2$-$CH_2$-$CH_2$—, —$CH_2$—O—C(O)—, —$CH_2$-C(O)—O—, —$CH_2$—NH—C(O)—, —$CH_2$—N($CH_3$)—C(O)—, —$CH_2$-C(O)—NH—, —NH($C_1$-$C_3$-alkyl), —N($C_1$-$C_3$-alkyl)$_2$, —$SO_2$($C_1$-$C_3$-alkyl), heterocyclyl, heteroaryl and R3;
  and, of these substituents, heterocyclyl and heteroaryl may in turn be at least monosubstituted by $C_1$-$C_3$-alkyl, $C_1$-$C_3$-alkoxy, fluorine, chlorine, bromine, trifluoromethyl, trifluoromethoxy or OH;

heteroaryl is pyridinyl, thienyl, pyrimidinyl, imidazolyl, furanyl, indolyl, benzimidazolyl, pyrazolyl, 1,3-benzodioxolyl, triazolyl, thiazolyl, isoxazolyl, pyrrolyl, pyrazinyl, oxazolyl, pyridazinyl, quinolinyl, isoquinolyl, benzofuranyl, 3-oxo-1,3-dihydroisobenzofuranyl or 4,5,6,7-tetrahydrobenzothiazolyl; and
heterocyclyl is morpholinyl, pyrrolidinyl, piperidinyl, tetrahydropyranyl, thiazolidinyl, dihydroisoxazolyl, piperazinyl or tetrahydrofuranyl;
or a physiologically tolerated salt thereof.

3. A compound as claimed in claim 2, in which the meanings in the formula (I) are:

X is a single bond, NH or $N(C_1-C_3\text{-alkyl})$;

R1 is hydrogen or $C_1-C_3$-alkyl which is optionally substituted by hydroxy, chlorine, methoxy or one, two or three fluorine atoms;

R2 is hydrogen, fluorine, —$OCF_3$, hydroxy, methoxy, —$NH_2$ or $C_1-C_3$-alkyl;

R3 is —$CH_2$—NR4R5, —$SO_2$NR4R5, —C(O)NR4R5, —$CH_2$—NHC(O)R6, —$CH_2$—$NHSO_2$R6 or —CH(OH)R7;

R4 and R5 are independently of one another selected from the group consisting of:
  hydrogen; unsubstituted or at least monosubstituted $C_1-C_{10}$-alkyl, $C_2-C_6$-alkenyl, phenyl, indanyl, heterocyclyl and heteroaryl,
    where the substituents are selected from the group consisting of: phenyl, heteroaryl, heterocyclyl, —O-phenyl, fluorine, —CN, —$C(O)NH_2$, —$C(O)(C_1-C_3$-alkyl), —C(O)-phenyl, —$N(C_1-C_3\text{-alkyl})_2$, —NH$(C_1-C_3$-alkyl), —$NH_2$, —NH-heteroaryl, —NH—C(O)-heteroaryl, $C_1-C_6$-alkyl, $C_1-C_3$-alkoxy and hydroxy,
    and the phenyl, heterocyclyl and heteroaryl fragments of these substituents may in turn be at least monosubstituted by fluorine, chlorine, bromine, oxo, —$CF_3$, —$OCF_3$, —$NO_2$, —CN, phenyl, pyrimidinyl, —$NHC(O)(C_1-C_3$-alkyl), —COOH, hydroxy, $C_1-C_3$-alkyl, $C_1-C_3$-alkoxy, —$SO_2NH_2$, —$SO_2NH(C_1-C_3$-alkyl), —$SO_2N(C_1-C_3\text{-alkyl})_2$, —$C(O)NH_2$, —$C(O)NH(C_1-C_3$-alkyl), —$C(O)N(C_1-C_3\text{-alkyl})_2$, —$SO_2(C_1-C_3$-alkyl), —$NH_2$, —NH$(C_1-C_3$-alkyl) or —$N(C_1-C_3\text{-alkyl})_2$; or
  R4 and R5 form together with the nitrogen atom to which they are bonded unsubstituted or at least monosubstituted heterocyclyl,
    where the substituents are selected from the group consisting of: phenyl, heteroaryl, heterocyclyl, oxo, fluorine, chlorine, —$C(O)(C_1-C_3$-alkyl), —C(O)-phenyl and hydroxy,
    and the phenyl, heterocyclyl and heteroaryl fragments of the substituents may in turn be at least monosubstituted by fluorine or $C_1-C_3$-alkyl;

R6 is $CF_3$ or unsubstituted or at least monosubstituted $C_1-C_6$-alkyl, pyridinyl, furanyl or phenyl,
  where the substituents are selected from the group consisting of: fluorine, —$NHC(O)(C_1-C_3$-alkyl), hydroxy $C_1-C_3$-alkyl, $C_1-C_3$-alkoxy and —O-pyridinyl;

R7 is selected from the group consisting of:
  hydrogen; unsubstituted or at least monosubstituted $C_1-C_6$-alkyl, phenyl and pyridinyl,
    where the substituents are selected from the group consisting of: fluorine, chlorine, bromine, hydroxy, $C_1-C_3$-alkyl and $C_1-C_3$-alkoxy;

Ar is unsubstituted or at least monosubstituted phenyl, thienyl, furanyl or pyridinyl,
  where the substituents are selected from the group consisting of: fluorine, chlorine, —$CF_3$, —$OCF_3$, C(O)$(C_1-C_3$-alkyl), —$NH_2$, —$NHC(O)(C_1-C_3$-alkyl), hydroxy, $C_1-C_3$-alkyl, $C_1-C_3$-alkoxy, —$CH_2$—$CH_2$—$CH_2$—, —$CH_2$—O—C(O)—, —$CH_2$-C(O)—O—, —$CH_2$—NH—C(O)—, —$CH_2$—N(CH_3)—C(O)—, —$CH_2$—C(O)—NH—, —NH$(C_1-C_3$-alkyl), —$N(C_1-C_3\text{-alkyl})_2$, —$SO_2(C_1-C_3$-alkyl) and R3;

heteroaryl is pyridinyl, thienyl, pyrimidinyl, imidazolyl, furanyl, indolyl, benzimidazolyl, pyrazolyl, 1,3-benzodioxolyl, triazolyl, thiazolyl, isoxazolyl, pyrrolyl, pyrazinyl, oxazolyl, pyridazinyl, quinolinyl, isoquinolyl, benzofuranyl, 3-oxo-1,3-dihydroisobenzofuranyl or 4,5,6,7-tetrahydrobenzothiazolyl; and heterocyclyl is morpholinyl, pyrrolidinyl, piperidinyl, tetrahydropyranyl, thiazolidinyl, dihydroxyisoxazolyl, piperazinyl or tetrahydrofuranyl;

or a physiologically tolerated salt thereof.

4. A compound as claimed in claim 3, in which the meanings in the formula (I) are:

X is a single bond, NH or $N(C_1-C_3\text{-alkyl})$;

R1 is hydrogen or $C_1-C_3$-alkyl;

R2 is hydrogen;

R3 is —$CH_2$—NR4R5, —$CH_2$—NHC(O)R6, —$CH_2$—$NHSO_2$R6, —C(O)NR4R5 or —CH(OH)R7;

R4 is selected from the group consisting of: hydrogen, unsubstituted or at least monosubstituted $C_1-C_{10}$-alkyl, $C_1-C_6$-alkenyl, phenyl, indanyl, heterocyclyl and heteroaryl,
  where the substituents are selected from the group consisting of: phenyl, heteroaryl, heterocyclyl, —O-phenyl, fluorine, —CN, —$C(O)NH_2$, —$C(O)(C_1-C_3$-alkyl), —C(O)-phenyl, —$N(C_1-C_3\text{-alkyl})_2$, —NH$(C_1-C_3$-alkyl), —$NH_2$, —NH-heteroaryl, —NH—C(O)-heteroaryl, $C_1-C_6$-alkyl, $C_1-C_3$-alkoxy and hydroxy,
  and the phenyl, heterocyclyl and heteroaryl fragments of these substituents may in turn by fluorine, chlorine, bromine, oxo, —$CF_3$, —$OCF_3$, —$NO_2$, —CN, phenyl, pyridinyl, —$NHC(O)(C_1-C_3$-alkyl), —COOH, hydroxy, $C_1-C_3$-alkyl, $C_1-C_3$-alkoxy, —$SO_2NH_2$, —$SO_2NH(C_1-C_3$-alkyl), —$SO_2N(C_1-C_3\text{-alkyl})_2$, —$C(O)NH_2$, —$C(O)NH(C_1-C_3$-alkyl), —$C(O)N(C_1-C_3\text{-alkyl})_2$, —$SO_2(C_1-C_3$-alkyl), —$NH_2$, —NH$(C_1-C_3$-alkyl) or —$N(C_1-C_3\text{-alkyl})_2$; and R5 is hydrogen; or R4 and R5 form together with the nitrogen atom to which they are bonded unsubstituted or at least monosubstituted heterocyclyl,
  where the substituents are selected from the group consisting of: phenyl, heteroaryl, heterocyclyl, oxo, fluorine, chlorine, —$C(O)(C_1-C_3$-alkyl), —C(O)-phenyl and hydroxy,
  and the phenyl, heterocyclyl and heteroaryl fragments of these substituents may in turn be at least monosubstituted by fluorine or $C_1-C_3$-alkyl;

R6 is $CF_3$ or unsubstituted or at least monosubstituted $C_1-C_6$-alkyl, pyridinyl, furanyl or phenyl,
  where the substituents are selected from the group consisting of: fluorine, —$NHC(O)(C_1-C_3$-alkyl), hydroxy, $C_1-C_3$-alkyl, $C_1-C_3$-alkoxy and —O-pyridinyl;

R7 is selected from the group consisting of:
  hydrogen; unsubstituted or at least monosubstituted $C_1-C_6$-alkyl, phenyl and pyridinyl,
    where the substituents are selected from the group consisting of: fluorine, chlorine, bromine, hydroxy, $C_1-C_3$-alkyl and $C_1-C_3$-alkoxy;

Ar is monosubstituted phenyl, thienyl, furanyl or pyridinyl,
  where the substituent is selected from the group consisting of: fluorine, chlorine, —$CF_3$, —$OCF_3$, —C(O)$(C_1-C_3$-alkyl), —$NH_2$, —$NHC(O)(C_1-C_3$-alkyl), hydroxy, $C_1-C_3$-alkyl, $C_1-C_3$-alkoxy, —NH$(C_1-C_3$-alkyl), —$N(C_1-C_3\text{-alkyl})_2$, —$SO_2(C_1-C_3$-alkyl) and R3;

and the substituent and X are in the meta position relative to one another;

heteroaryl is pyridinyl, thienyl, pyrimidinyl, imidazolyl, furanyl, benzimidazolyl, pyrazolyl, thiazolyl, isoxazolyl, pyrrolyl, pyrazinyl, 3-oxo-1,3-dihydroisobenzofuranyl or 4,5,6,7-tetrahydrobenzothiazolyl; and heterocyclyl is morpholinyl, pyrrolidinyl, piperidinyl, tetrahydropyranyl, thiazolidinyl, dihydroisoxazolyl, piperazinyl or tetrahydrofuranyl;

or a physiologically tolerated salt thereof.

5. A compound as claimed in claim 4, in which the meanings in the formula (I) are:

X is a single bond or NH;
R1 is hydrogen or $C_1$-$C_3$-alkyl;
R2 is hydrogen;
R3 is —$CH_2$—NR4R5, —C(O)NR4R5 or —CH(OH)R7;
R4 is selected from the group consisting of: hydrogen; unsubstituted or at least monosubstituted $C_1$-$C_{10}$-alkyl, cyclohexenyl, indanyl, phenyl, pyrrolidinyl, pyrrolyl, pyrazolyl, furanyl and piperidinyl,
  where the substituents are selected from the group consisting of: fluorine, —CN, —C(O)$NH_2$, —O-phenyl, —C(O)-phenyl, —N($CH_3$)$_2$, $C_1$-$C_3$-alkyl, $C_1$-$C_3$-alkoxy, hydroxy, unsubstituted or at least monosubstituted phenyl, pyridinyl, thienyl, pyrimidinyl, imidazolyl, furanyl, indolyl, benzimidazolyl, pyrazolyl, morpholinyl, pyrrolidinyl, 1,3-benzodioxolyl, piperidinyl, tetrahydropyranyl, triazolyl, thiazolyl, thiazolidinyl, isoxazolyl and dihydroisoxazolyl, the substituents of which are in turn selected from the group consisting of: fluorine, chlorine, oxo, $CF_3$, —$OCF_3$, —$NO_2$, phenyl, pyridinyl, —NHC(O)$CH_3$, —COOH, hydroxy, $C_1$-$C_3$-alkyl, $C_1$-$C_3$-alkoxy, —$SO_2NH_2$, —C(O)$NH_2$ and —N($CH_3$)$_2$; and R5 is hydrogen; or
R4 and R5 form together with the nitrogen atom to which they are bonded a radical selected from the group consisting of: unsubstituted or at least monosubstituted piperidinyl, pyrrolidinyl, morpholinyl and piperazinyl,
  where the substituents are selected from the group consisting of: fluorine, —C(O)($C_1$-$C_3$-alkyl), oxo, $C_1$-$C_3$-alkyl, hydroxy, unsubstituted or at least monosubstituted phenyl, imidazolyl, pyridinyl, pyrimidinyl, piperidinyl and pyrrolidinyl, the substituents of which are in turn fluorine or $C_1$-$C_3$-alkyl;
R7 is hydrogen; and
Ar is monosubstituted phenyl, thienyl, furanyl or pyridinyl, where the substituent is selected from the group consisting of:
  fluorine, chlorine, —$CF_3$, —$OCF_3$, —C(O)($C_1$-$C_3$-alkyl), —$NH_2$, —NHC(O)($C_1$-$C_3$-alkyl), hydroxy, $C_1$-$C_3$-alkyl, $C_1$-$C_3$-alkoxy, —NH($C_1$-$C_3$-alkyl), —N($C_1$-$C_3$-alkyl)$_2$, —$SC_2$($C_1$-$C_3$-alkyl) and R3;
  and the substituent and X are in the meta position relative to one another;

or a physiologically tolerated salt thereof.

6. A compound as claimed in claim 5, in which the meanings in the formula (I) are:

X is a single bond or NH;
R1 is hydrogen or $C_1$-$C_3$-alkyl;
R2 is hydrogen;
R3 is —$CH_2$—NR4R5;
R4 is unsubstituted or at least monosubstituted $C_1$-$C_6$-alkyl,
  where the substituents are selected from the group consisting of: —N($CH_3$)$_2$, hydroxy, unsubstituted or at least monosubstituted phenyl, pyridinyl, imidazolyl, indolyl, benzimidazolyl, pyrazolyl and pyrrolidinyl, the substituents of which are in turn selected from the group consisting of:
    —NHC(O)$CH_3$, $C_1$-$C_3$-alkyl, $C_1$-$C_3$-alkoxy, —$SO_2NH_2$ and —C(O)$NH_2$; and R5 is hydrogen; or
R4 and R5 form together with the nitrogen atom to which they are bonded a radical selected from the group consisting of:
  unsubstituted or at least monosubstituted pyrrolidinyl, piperidinyl and piperazinyl,
  where the substituents are selected from the group consisting of:
    $C_1$-$C_3$-alkyl, hydroxy and pyrrolidinyl; and
Ar is monosubstituted phenyl, thienyl, furanyl or pyridinyl, where the substituent is selected from the group consisting of:
  fluorine, chlorine, —$OCF_3$, —C(O)$CH_3$, —NHC(O)$CH_3$, hydroxy, —N($CH_3$)$_2$, ethoxy, —$SO_2CH_3$ and R3;
  and the substituent and X are in the meta position relative to one another;

or a physiologically tolerated salt thereof.

7. A compound as claimed in claim 5, selected from the group consisting of:
  4-(3-methanesulfonylphenylamino)-3-methyl-5,6,7,8-tetrahydro-2H-isoquinolin-1-one,
  4-(3-acetylphenylamino)-3-methyl-5,6,7,8-tetrahydro-2H-isoquinolin-1-one,
  4-(5-butylaminomethylfuran-2-yl)-3-methyl-5,6,7,8-tetrahydro-2H-isoquinolin-1-one,
  3-methyl-4-(5-pyrrolidin-1-ylmethylfuran-2-yl)-5,6,7,8-tetrahydro-2H-isoquinolin-1-one,
  4-[5-(3-hydroxypyrrolidin-1-ylmethyl)furan-2-yl]-5,6,7,8-tetrahydro-2H-isoquinolin-1-one,
  4-(5-{[(4-pyrrolidin-1-ylpiperidin-1-ylmethyl)amino]methyl}furan-2-yl)-5,6,7,8-tetrahydro-2H-isoquinolin-1-one, 4-(5-{[2-dimethylaminoethylamino)methyl]furan-2-yl)-5, 6,7,8-tetrahydro-2H-isoquinolin-1-one,
  4-{5-[(2-hydroxy-2-phenylethylamino)methyl]furan-2-yl}-5,6,7,8-tetrahydro-2H-isoquinolin-1-one,
  4-(5-{[(4-methylpiperazin-1-ylmethyl)amino]methyl}furan-2-yl)- 5,6,7,8-tetrahydro-2H-isoquinolin-1-one, 4-(5-{[(1-methyl-1H-pyrazol-4-ylmethyl)-amino ]methyl}furan-2-yl)-5,6,7,8-tetrahydro-2H-isoquinolin-1-one,
  4-(5-butylaminomethylfuran-2-yl)-5,6,7,8-tetrahydro-2H-isoquinolin-1-one and
  4-(5-hydroxymethylfuran-2-yl)-3-methyl-5,6,7,8-tetrahydro-2H-isoquinolin-1-one;

or a physiologically tolerated salt thereof.

8. A pharmaceutical composition comprising an effective amount of at least one compound as claimed in claim 1 and a physiologically acceptable carrier.

9. A pharmaceutical composition as claimed in claim 8, wherein the pharmaceutical composition is in the form of a pill, tablet, coated tablet, suckable tablet, granules, capsule, hard or soft gelatin capsule, aqueous solution, alcoholic solution, oily solution, syrup, emulsion, suspension, suppository, pastille, solution for injection or infusion, ointment, tincture, cream, lotion, dusting powder, spray, transdermal therapeutic system, nasal spray, aerosol, aerosol mixture, microcapsule, implant, rod or patch.

10. A method for preparing a compound of the formula (Ib),

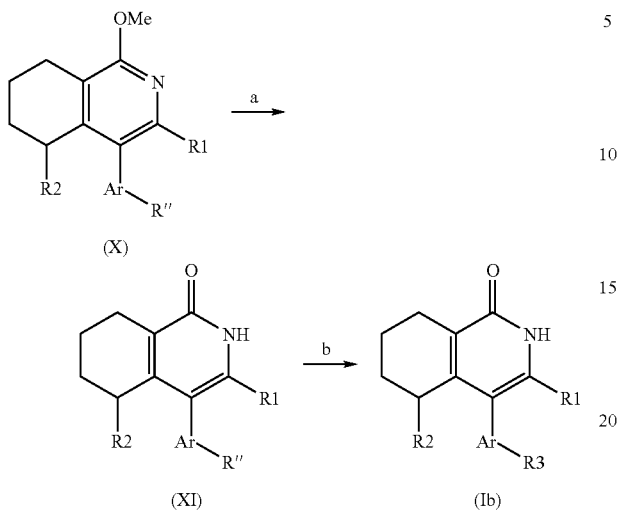

a a compound of the formula (X) is reacted with a suitable reagent, with elimination of the methyl group, to give the compound of the formula (XI), and
b the compound of formula (XI)

(1) is reacted with a suitable amine in the presence of a reducing agent when R" is —CHO and R3 is —CH$_2$—NR4R5, or
(2) is reduced with a suitable reducing agent when R" is —CHO and R3 is —CH$_2$OH, or
(3) is reacted by reductive amination with ammonium acetate, with subsequent coupling reaction with a suitable acid chloride, a suitable acid or a suitable sulfonyl chloride when R" is —CHO and R3 is —CH$_2$NHC(O)R6 or —CH$_2$NHSO$_2$R6, or
(4) is reacted with a suitable amine in the presence of a condensing agent when R" is —COOH and R3 is —C(O)NR4R5, wherein R1 is hydrogen, fluorine, chlorine, —CN, methoxy, —OCF3 or C1-C3-alkyl which is optionally substituted by hydroxy, chlorine, methoxy or one, two or three fluorine atoms;

R2 is hydrogen, fluorine, —CN, hydroxy, methoxy, —OCF3, —NH2, —NH(C1—C3-alkyl), —N(C1-C3-alkyl)2 or C1-C3-alkyl which is optionally substituted by hydroxy, chlorine, methoxy or one, two or three fluorine atoms;

R3 is —(C1-C3-alkyl)—NR4R5, —SO2NR4R5, —C(O)NR4R5, —C(H)=N—OR9, —C(O)R6, —NHC(O)R6, —(C1-C3-alkyl)—NHC(O)R6, —NHSO2R6, —(C1-C3-alkyl)—NHSO2R6 or —CH(OH)R7;

R4 and R5 are independently of one another selected from the group consisting of:
hydrogen; unsubstituted or at least monosubstituted C1-C10-alkyl, C2-C6-alkenyl, C2-C6-alkynyl, aryl, heteroaryl and heterocyclyl,
where the substituents are selected from the group consisting of: aryl, heteroaryl, heterocyclyl, —O-aryl, fluorine, chlorine, bromine, —CF3, —OCF3, —NO2, —CN, —C(O)R8, —NHC(O)(C1-C3-alkyl), —NH2, hydroxy, C1-C6-alkyl, C1-C3-alkoxy, —NH(C1-C3-alkyl), —N(C1-C3-alkyl)2, —NH-aryl, —NH-heteroaryl, —NH—C(O)-heteroaryl, —SO2NH2, —SO2(C1-C3-alkyl) and —NH—SO2(C1-C3-alkyl),
and the aryl, heteroaryl and heterocyclyl fragments of these substituents may in turn be at least monosubstituted by fluorine, chlorine, bromine, oxo, —CF3, —OCF3, —NO2, —CN, aryl, heteroaryl, —NHC(O)(C1-C3-alkyl), —COOH, hydroxy, C1-C3-alkyl, C1-C3-alkoxy, —SO2NH2, —SO2NH(C1-C3-alkyl), —SO2N(C1-C3-alkyl)2, —C(O)NH2, —C(O)NH(C1-C3-alkyl), —C(O)N(C1-C3-alkyl)2, —SO2(C1-C3-alkyl), —NH2, —NH(C1-C3-alkyl) or —N(C1-C3-alkyl)2; or R4 and R5 form together with the nitrogen atom to which they are bonded unsubstituted or at least monosubstituted heterocyclyl,
where the substituents are selected from the group consisting of: aryl, heteroaryl, heterocyclyl, oxo, fluorine, chlorine, bromine, —CF3, —OCF3, —NO2, —CN, —C(O)R8, —NHC(O)(C1-C3-alkyl), —NH2, hydroxy, C1-C3-alkyl, C1-C3-alkoxy, —NH(C1-C3-alkyl), —N(C1-C3-alkyl)2, —SO2NH2, —SO2(C1-C3-alkyl) and —NH—SO2(C1-C3-alkyl),
and, of these substituents, aryl, heterocyclyl and heteroaryl in turn may be at least monosubstituted by fluorine, chlorine, bromine, hydroxy, C1-C3-alkyl or C1-C3-alkoxy;

R6 is unsubstituted or at least monosubstituted C1-C6-alkyl, phenyl, heteroaryl or heterocyclyl,
where the substituents are selected from the group consisting of: fluorine, chlorine, bromine, aryl, heterocyclyl, heteroaryl, —CF3, —OCF3, —NO2, —CN, —C(O)R8, —NHC(O)(C1-C3-alkyl), —NH2, hydroxy, C1-C3-alkyl, C1-C3-alkoxy, —O-heteroaryl, —O-aryl, —NH(C1-C3-alkyl), —N(C1-C3-alkyl)2, —SO2NH2, —SO2(C1-C3-alkyl) and —NH—SO2(C1—3-alkyl),
and the aryl, heterocyclyl and heteroaryl fragments of these substituents may in turn be at least monosubstituted by fluorine, chlorine, bromine, hydroxy, C1-C3-alkyl or C1-C3-alkoxy;

R7 is selected from the group consisting of:
hydrogen; unsubstituted or at least monosubstituted C1-C6-alkyl, phenyl and heteroaryl,
where the substituents are selected from the group consisting of:
fluorine, chlorine, bromine, —CF3, —OCF3, —NO2, —CN, —C(O)R8, —NHC(O)(C1-C3-alkyl), —NH2, hydroxy, C1-C3-alkyl, C1-C3-alkoxy, —NH(C1-C3-alkyl), —N(C1-C3-alkyl)2, —SO2NH2, —SO2(C1-C3-alkyl) and —NH—SO2(C1-C3-alkyl);

R8 is C1-C3-alkoxy, —O-phenyl, C1-C3-alkyl, —NH2, —NH(C1-C3-alkyl), —N(C1-C3-alkyl)2 or phenyl,
and the above phenyl fragments may in turn be at least monosubstituted by fluorine, chlorine, bromine, oxo, —CF$_3$, —OCF$_3$, —NO$_2$, —CN, aryl, heteroaryl, —NHC(O)(C$_1$-C$_3$-alkyl), —COOH, hydroxy, C$_1$-C$_3$-alkyl, C$_1$-C$_3$-alkoxy, —SO$_2$NH$_2$, —SO$_2$NH(C$_1$-C$_3$-alkyl), —SO$_2$N(C$_1$-C$_3$-alkyl)$_2$, —C(O)NH$_2$, —C(O)NH(C$_1$-C$_3$-alkyl), —C(O)N(C$_1$-C$_3$-alkyl)$_2$, —SO$_2$(C$_1$-C$_3$-alkyl), —NH$_2$, —NH(C$_1$-C$_3$-alkyl) or —N(C$_1$-C$_3$-alkyl)2;

R9 is selected from the group consisting of:
hydrogen; unsubstituted or at least monosubstituted C$_1$-C$_6$-alkyl and phenyl, where the substituents are selected from the group consisting of:

fluorine, chlorine, bromine, aryl, heterocyclyl, heteroaryl, —CF3, —OCF3, —NO2, —CN, —C(O)R8, —NHC(O)(C1-C3-alkyl), C1-C3-alkyl, C1-C3-alkoxy, —NH(C1-C3-alkyl), —N(C1-C3-alkyl)2, —SO2NH2, —SO2(C1-C3-alkyl) and —NH—SO2(C1-C3-alkyl), and, of these substituents, aryl, heterocyclyl and heteroaryl may in turn be at least monosubstituted by fluorine, chlorine, bromine, C1-C3-alkyl or C1-C3-alkoxy;

Ar is unsubstituted or at least monosubstituted aryl or heteroaryl, where the substituents are selected from the group consisting of: fluorine, chlorine, bromine, —CF3, —OCF3, —NO2, —CN, —C(O)R8, —NH2, —NHC(O)(C1—C6-alkyl), hydroxy, C1-C6-alkyl, C1-C6-alkoxy, —CH2—CH2—CH2—, —CH2—O—C(O)—, —CH2-C(O)—O—, —CH2—NH—C(O)—, —CH2—N(CH3)—C(O)—, —CH2-C(O)—NH—, —NH(C1-C6-alkyl), —N(C1-C6-alkyl)2, —SO2(C1-C6-alkyl), heterocyclyl, heteroaryl, aryl and R3, and, of these substituents, heterocyclyl, aryl and heteroaryl may in turn be at least monosubstituted by C1-C6-alkyl, C1-C6-alkoxy, fluorine, chlorine, bromine, trifluoromethyl, trifluoromethoxy or OH;

heteroaryl is a 5 to 10-membered, aromatic, mono- or bicyclic heterocycle which comprises one or more heteroatoms selected from N, O and S;

aryl is a 5 to 10-membered, aromatic, mono- or bicycle; and heterocyclyl is a 5 to 10-membered, non-aromatic, mono- or bicyclic heterocycle which comprises one or more heteroatoms selected from N, O and S.

\* \* \* \* \*

UNITED STATES PATENT AND TRADEMARK OFFICE
CERTIFICATE OF CORRECTION

PATENT NO. : 7,795,278 B2
APPLICATION NO. : 11/567352
DATED : September 14, 2010
INVENTOR(S) : Stefan Peukert et al.

It is certified that error appears in the above-identified patent and that said Letters Patent is hereby corrected as shown below:

On the Title page, in item (56), in column 2, under "Other Publications", line 3, delete "Perparation" and insert -- Preparation --, therefor.

In column 1, line 6, delete "FIELD OF THE INVENTION" and insert the same on Col. 1, Line 7 as a heading.

In column 14, line 7, delete "tetrahydrobenzothiazolyl" and insert -- tetrahydrobenzothiazolyl; --, therefor.

In column 21, line 43, delete "Xi" and insert -- XI --, therefor.

In column 21, line 58, delete "Xi" and insert -- XI --, therefor.

In column 21, line 62, delete "Xi" and insert -- XI --, therefor.

In column 22, line 29, delete "Xi" and insert -- XI --, therefor.

In column 22, line 35, delete "above-mentioned" and insert -- abovementioned --, therefor.

In column 27, line 34, delete "tetramethylfluoroamindinium" and insert -- tetramethylfluoroamidinium --, therefor.

In column 33, line 63, delete "procedure" and insert -- procedure. --, therefor.

In column 41, line 25, delete "H, 3.20," and insert -- H; 3.20, --, therefor.

In column 41, line 35, delete "H, 6.63-6.55," and insert -- H; 6.63-6.55, --, therefor.

Signed and Sealed this
Twenty-fourth Day of May, 2011

David J. Kappos
*Director of the United States Patent and Trademark Office*

CERTIFICATE OF CORRECTION (continued)
U.S. Pat. No. 7,795,278 B2

In column 41, line 36, delete "H, 3.08," and insert -- H; 3.08, --, therefor.

In column 47, line 46, in example 71, delete "({[4-" and insert -- ([4- --, therefor.

In column 54, line 41, in claim 1, delete "chlorine" and insert -- chlorine, --, therefor.

In column 55, line 5, in claim 1, delete "—N($C_1$-$C_3$-alkyl)$_2$" and insert-- —N($C_1$-$C_3$-alkyl)$_2$; --, therefor.

In column 55, line 44, in claim 1, delete "thereof." and insert -- thereof; --, therefor.

In column 57, line 10, in claim 3, delete "—$CH_2$—$NHSO_2R6$" and insert -- —$CH_2NHSO_2R6$ --, therefor.

In column 57, line 27, in claim 3, delete "pyrimidinyl," and insert -- pyridinyl, --, therefor.

In column 59, line 17, in claim 5, delete "of;" and insert -- of: --, therefor.

In column 60, line 42, in claim 7, delete "2-yl)" and insert -- 2-yl} --, therefor.